US012799463B2

(12) United States Patent
Kim et al.

(10) Patent No.: US 12,799,463 B2
(45) Date of Patent: Nov. 17, 2026

(54) GAMMA-AMINOBUTYRATE PERMEASE VARIANT AND METHOD FOR PRODUCING ISOLEUCINE USING THE SAME

(71) Applicant: CJ CHEILJEDANG CORPORATION, Seoul (KR)

(72) Inventors: Kyungrim Kim, Seoul (KR); Jihyun Shim, Seoul (KR); Heeyeong Kim, Seoul (KR); Woosung Choi, Seoul (KR); Kwang Woo Lee, Seoul (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 535 days.

(21) Appl. No.: 18/266,447

(22) PCT Filed: Dec. 8, 2021

(86) PCT No.: PCT/KR2021/018520
§ 371 (c)(1),
(2) Date: Jun. 9, 2023

(87) PCT Pub. No.: WO2022/124786
PCT Pub. Date: Jun. 16, 2022

(65) Prior Publication Data

US 2024/0110161 A1 Apr. 4, 2024

(30) Foreign Application Priority Data

Dec. 11, 2020 (KR) ........................ 10-2020-0173743

(51) Int. Cl.
*C12N 9/10* (2006.01)
*C12P 13/06* (2006.01)

(52) U.S. Cl.
CPC ................ *C12N 9/10* (2013.01); *C12P 13/06* (2013.01)

(58) Field of Classification Search
CPC ........................................................ C12N 9/10
See application file for complete search history.

(56) References Cited

U.S. PATENT DOCUMENTS

| | | | |
|---|---|---|---|
| 4,656,135 | A | 4/1987 | Tsuchida et al. |
| 6,072,083 | A | 6/2000 | Hasegawa et al. |
| 7,662,943 | B2 | 2/2010 | Park et al. |
| 10,113,190 | B2 | 10/2018 | Gerstmeir et al. |
| 10,273,491 | B2 | 4/2019 | Lee et al. |
| 10,584,338 | B2 | 3/2020 | Lee et al. |
| 10,662,450 | B2 | 5/2020 | Kim et al. |
| 2002/0197605 | A1 | 12/2002 | Nakagawa et al. |

FOREIGN PATENT DOCUMENTS

| | | | |
|---|---|---|---|
| DE | 19523279 A1 | 1/1997 | |
| JP | H08-047397 A | 2/1996 | |
| KR | 10-2006-0084446 A | 7/2006 | |
| KR | 10-1335789 B1 | 12/2013 | |
| KR | 10-2015-0113965 A | 10/2015 | |
| KR | 10-2017-0047725 A | 5/2017 | |
| KR | 10-1751967 B1 | 6/2017 | |
| KR | 10-1996769 B1 | 10/2019 | |
| KR | 10-2020-0136813 A | 12/2020 | |
| KR | 10-2022-0000705 A | 1/2022 | |

OTHER PUBLICATIONS

Q8VKK1. UniProtKB/TrEMBL. Apr. 15, 2025.*
Wehrmann (Functional analysis of sequences adjacent to dapE of Corynebacterium glutamicum reveals the presence of aroP, which encodes the aromatic amino acid transporter. J Bacteriol. Oct. 1995; 177(20):5991-3. (Year: 1995).*
Fransceus (J Ind Microbiol Biotechnol. May 2017;44(4-5):687-695 (Year: 2017).*
Sanavia (Computational and Structural Biotechnology Journal, vol. 18, 2020, pp. 1968-1979. (Year: 2020).*
Studer (Residue mutations and their impact on protein structure and function: detecting beneficial and pathogenic changes. Biochem. J. (2013) 449, 581-594. (Year: 2013).*
AROP_CORGL (UniprotKB/Swiss-Prot Database. Dec. 2, 2020. (Year: 2020).*
Zaprasis, et al., "The y-Aminobutyrate Permease GabP Serves as the Third Proline Transporter of Bacillus subtilis", Feb. 2014, Journal of Bacteriology, vol. 196, Issue 3, p. 515-526.
"Amino acid transporter [Corynebacterium glutamicum]", Dec. 2016, 2 pages total, https://www.ncbi.nlm.nih.gov/protein/OKX83310.1.
"Amino acid transporter [Corynebacterium glutamicum]", Apr. 2017, 2 pages total, https://www.ncbi.nlm.nih.gov/protein/ANU33332.1.
"Gamma-aminobutyrate permease [Corynebacterium jelkeium K411]", Mar. 2015, 2 pages total, https://www.ncbi.nlm.nih.gov/protein/CAI38123.1.
Office Action issued Jun. 11, 2024 for Japanese Patent Application No. 2023-535385.
NCBI, GenBank accession No. WP_011014125.1, aromatic amino acid transport protein AroP [*Corynebacterium glutamicum*] (Aug. 31, 2020).
Wang, "Strategy for improving L-isoleucine production efficiency in Corynebacterium glutamicum," Applied Microbiology and Biotechnology, 103: 2101-2111 (2019).
Nakashima et al., "Bacterial Cellular Engineering by Genome Editing and Gene Silencing," Int. J. Mol. Sci., 15(2):2773-2793 (2014).
Nair, "Introduction to Biotechnology and Genetic Engineering," Infinity Science Press LLC (2008).

(Continued)

*Primary Examiner* — Yong D Pak
(74) *Attorney, Agent, or Firm* — Morgan, Lewis & Bockius LLP

(57) ABSTRACT

The present application relates to a novel γ-aminobutyrate permease variant that decreases the amount of by-products generated during the production of L-isoleucine, a polynucleotide encoding the variant, and a vector comprising the polynucleotide, a microorganism comprising the variant, polynucleotide or vector, and a method for producing L-isoleucine using the microorganism.

20 Claims, No Drawings

Specification includes a Sequence Listing.

(56) References Cited

OTHER PUBLICATIONS

International Search Report issued in corresponding International Patent Application No. PCT/KR2021/018520 dated Mar. 10, 2022.
Tauch, et al., "Complete Genome Sequence and Analysis of the Multiresistant Nosocomial Pathogen Corynebacterium jeikeium K411, a Lipid-Requiring Bacterium of the Human Skin Flora", 2005, Journal of Bacteriology, vol. 187, No. 13, p. 4671-4682, XP 007904509.
Honore, et al., "Nucleotide sequence of the aroP gene encoding the general aromatic amino acid transport protein of *Escherichia coli* K-12: homology with yeast transport proteins", 1990, Nucleic Acids Research, vol. 18, Issue 3, p. 653, XP 093140475.
Extended European Search Report issued Apr. 15, 2024 for European Patent Application No. 21903832.0.

* cited by examiner

SEQUENCE LISTING

```
<160> NUMBER OF SEQ ID NOS: 25

<210> SEQ ID NO 1
<211> LENGTH: 463
<212> TYPE: PRT
<213> ORGANISM: Unknown
<220> FEATURE:
<223> OTHER INFORMATION: aroP

<400> SEQUENCE: 1

Met Ala Lys Ser Asn Glu Gly Leu Gly Thr Gly Leu Arg Thr Arg His
1               5                   10                  15

Leu Thr Met Met Gly Leu Gly Ser Ala Ile Gly Ala Gly Leu Phe Leu
            20                  25                  30

Gly Thr Gly Val Gly Ile Arg Ala Ala Gly Pro Ala Val Leu Leu Ala
        35                  40                  45

Tyr Ile Ile Ala Gly Ala Ile Val Val Leu Val Met Gln Met Leu Gly
    50                  55                  60
```

```
Glu Met Ala Ala Ala Arg Pro Ala Ser Gly Ser Phe Ser Arg Tyr Gly
65                  70                  75                  80

Glu Asp Ala Phe Gly His Trp Ala Gly Phe Ser Leu Gly Trp Leu Tyr
                85                  90                  95

Trp Phe Met Leu Ile Met Val Met Gly Ala Glu Met Thr Gly Ala Ala
            100                 105                 110

Ala Ile Met Gly Ala Trp Phe Gly Val Glu Pro Trp Ile Pro Ser Leu
        115                 120                 125

Val Cys Val Val Phe Phe Ala Val Val Asn Leu Val Ala Val Arg Gly
    130                 135                 140

Phe Gly Glu Phe Glu Tyr Trp Phe Ala Phe Ile Lys Val Ala Val Ile
145                 150                 155                 160

Ile Ala Phe Leu Ile Ile Gly Ile Ala Leu Ile Phe Gly Trp Leu Pro
                165                 170                 175

Gly Ser Thr Phe Val Gly Thr Ser Asn Phe Ile Gly Asp His Gly Phe
            180                 185                 190

Met Pro Asn Gly Ile Ser Gly Val Ala Ala Gly Leu Leu Ala Val Ala
        195                 200                 205

Phe Ala Phe Gly Gly Ile Glu Ile Val Thr Ile Ala Ala Ala Glu Ser
    210                 215                 220

Asp Lys Pro Arg Glu Ala Ile Ser Leu Ala Val Arg Ala Val Ile Trp
225                 230                 235                 240

Arg Ile Ser Val Phe Tyr Leu Gly Ser Val Leu Val Ile Thr Phe Leu
                245                 250                 255

Met Pro Tyr Glu Ser Ile Asn Gly Ala Asp Thr Ala Ala Glu Ser Pro
            260                 265                 270

Phe Thr Gln Ile Leu Ala Met Ala Asn Ile Pro Gly Thr Val Gly Phe
        275                 280                 285

Met Glu Ala Ile Ile Val Leu Ala Leu Leu Ser Ala Phe Asn Ala Gln
    290                 295                 300

Ile Tyr Ala Thr Ser Arg Leu Val Phe Ser Met Ala Asn Arg Gln Asp
305                 310                 315                 320

Ala Pro Arg Val Phe Ser Lys Leu Ser Thr Ser His Val Pro Thr Asn
                325                 330                 335

Ala Val Leu Leu Ser Met Phe Phe Ala Phe Val Ser Val Gly Leu Gln
            340                 345                 350

Tyr Trp Asn Pro Ala Gly Leu Leu Asp Phe Leu Leu Asn Ala Val Gly
        355                 360                 365

Gly Cys Leu Ile Val Val Trp Ala Met Ile Thr Leu Ser Gln Leu Lys
    370                 375                 380

Leu Arg Lys Glu Leu Gln Ala Asn Asp Glu Ile Ser Thr Val Arg Met
385                 390                 395                 400

Trp Ala His Pro Trp Leu Gly Ile Leu Thr Leu Val Leu Leu Ala Gly
                405                 410                 415

Leu Val Ala Leu Met Leu Gly Asp Ala Ala Ser Arg Ser Gln Val Tyr
            420                 425                 430

Ser Val Ala Ile Val Tyr Gly Phe Leu Val Leu Leu Ser Phe Val Thr
        435                 440                 445

Val Asn Ser Pro Leu Arg Gly Gly Arg Thr Pro Ser Asp Leu Asn
    450                 455                 460
```

<210> SEQ ID NO 2
<211> LENGTH: 1392
<212> TYPE: DNA

<213> ORGANISM: Unknown
<220> FEATURE:
<223> OTHER INFORMATION: aroP

<400> SEQUENCE: 2
atggctaaat ctaatgaagg gctgggaacc ggacttcgga cccgccacct cacaatgatg 60
ggactcggct ccgcaattgg tgccggactg ttcctcggca ccggcgttgg tatccgcgca 120
gccggccccg cagtgctcct ggcgtacatc atcgccggag ccatcgttgt gcttgttatg 180
caaatgctcg gcgagatggc tgctgcccgt cccgcctccg gatcgttttc acgttacggc 240
gaggatgctt tcggccactg ggctggtttc tccctcggtt ggttgtactg gttcatgctg 300
attatggtga tgggcgccga aatgactggc gctgctgcca tcatgggtgc atggttcggc 360
gtcgaaccgt ggattccttc gcttgtctgc gtggtcttct tcgctgtggt gaacctcgtc 420
gcggttcgcg gtttcggtga attcgagtac tggttcgcat tcattaaggt cgcggtgatc 480
atcgctttcc tcatcattgg tattgctctt attttcggat ggcttcccgg atccaccttt 540
gttggaacct caaacttcat cggtgatcac ggattcatgc ccaatggtat ttctggtgtt 600
gctgctggtt tgctcgcggt ggcttttgcc tttggtggca ttgaaattgt caccattgca 660
gctgcagagt ccgataagcc acgtgaagct atttccctgg cggtgcgtgc cgtgatttgg 720
cgtatttcag tcttttactt gggctctgtt ttggtcatca ctttcctcat gccttatgag 780
tcgatcaatg gtgccgacac cgctgcggaa tccccccttca cccaaatcct ggcgatggca 840
aacatccctg gcacggttgg tttcatggaa gcgatcatcg ttctagcact gctttccgct 900
ttcaacgccc aaatctatgc cacttctcgt ttggtatttt ccatggcgaa tcgacaagac 960
gctccgcgag ttttcagtaa gctcagcacc agccacgtcc ccaccaatgc ggtgctgttg 1020
tccatgttct tcgccttcgt ttcagttggt ttgcagtact ggaatccagc cggtctgctt 1080
gatttcctcc tcaacgctgt tggcggttgt ttgattgtgg tgtgggcaat gatcactttg 1140
tcacagttga aactccgcaa agaactgcaa gcaaacgatg aaatctccac ggttcgcatg 1200
tgggcgcacc catggttagg catcctcacc ttggttttgt tggcaggact cgttgctctc 1260
atgctcggcg acgcagcctc ccgcagccag gtttactcag tggcaattgt gtacggattc 1320
ttggttcttt tgtccttcgt cacagttaac agcccattgc gcggaggtcg cacccccttcc 1380 gacttgaact ga 1392

<210> SEQ ID NO 3
<211> LENGTH: 463
<212> TYPE: PRT
<213> ORGANISM: Unknown
<220> FEATURE:
<223> OTHER INFORMATION: aroP

<400> SEQUENCE: 3

Met Ala Lys Ser Asn Glu Gly Leu Gly Thr Gly Leu Arg Thr Arg His
1 5 10 15

Leu Thr Met Met Gly Leu Gly Ser Ala Ile Gly Ala Gly Leu Phe Leu
20 25 30

Gly Thr Gly Val Gly Ile Arg Ala Ala Gly Pro Ala Val Leu Leu Ala
35 40 45

Tyr Ile Ile Ala Gly Ala Ile Val Val Leu Val Met Gln Met Leu Gly
50 55 60

Glu Met Ala Ala Ala Arg Pro Ala Ser Gly Ser Phe Ser Arg Tyr Gly
65 70 75 80

-continued

Glu Asp Ala Phe Gly His Trp Ala Gly Phe Ser Leu Gly Trp Leu Tyr
85 90 95

Trp Phe Met Leu Ile Met Val Met Gly Ala Glu Met Thr Gly Ala Ala
100 105 110

Ala Ile Met Gly Ala Trp Phe Gly Val Glu Pro Trp Ile Pro Ser Leu
115 120 125

Val Cys Val Val Phe Phe Ala Val Val Asn Leu Val Ala Val Arg Gly
130 135 140

Phe Gly Glu Phe Glu Tyr Trp Phe Ala Phe Ile Lys Val Ala Val Ile
145 150 155 160

Ile Ala Phe Leu Ile Ile Gly Ile Ala Leu Ile Phe Gly Trp Leu Pro
165 170 175

Gly Ser Thr Phe Val Gly Thr Ser Asn Phe Ile Gly Asp His Gly Phe
180 185 190

Met Pro Asn Gly Ile Ser Gly Val Ala Ala Gly Leu Leu Ala Val Ala
195 200 205

Phe Ala Phe Thr Gly Ile Glu Ile Val Thr Ile Ala Ala Ala Glu Ser
210 215 220

Asp Lys Pro Arg Glu Ala Ile Ser Leu Ala Val Arg Ala Val Ile Trp
225 230 235 240

Arg Ile Ser Val Phe Tyr Leu Gly Ser Val Leu Val Ile Thr Phe Leu
245 250 255

Met Pro Tyr Glu Ser Ile Asn Gly Ala Asp Thr Ala Ala Glu Ser Pro
260 265 270

Phe Thr Gln Ile Leu Ala Met Ala Asn Ile Pro Gly Thr Val Gly Phe
275 280 285

Met Glu Ala Ile Ile Val Leu Ala Leu Leu Ser Ala Phe Asn Ala Gln
290 295 300

Ile Tyr Ala Thr Ser Arg Leu Val Phe Ser Met Ala Asn Arg Gln Asp
305 310 315 320

Ala Pro Arg Val Phe Ser Lys Leu Ser Thr Ser His Val Pro Thr Asn
325 330 335

Ala Val Leu Leu Ser Met Phe Phe Ala Phe Val Ser Val Gly Leu Gln
340 345 350

Tyr Trp Asn Pro Ala Gly Leu Leu Asp Phe Leu Leu Asn Ala Val Gly
355 360 365

Gly Cys Leu Ile Val Val Trp Ala Met Ile Thr Leu Ser Gln Leu Lys
370 375 380

Leu Arg Lys Glu Leu Gln Ala Asn Asp Glu Ile Ser Thr Val Arg Met
385 390 395 400

Trp Ala His Pro Trp Leu Gly Ile Leu Thr Leu Val Leu Leu Ala Gly
405 410 415

Leu Val Ala Leu Met Leu Gly Asp Ala Ala Ser Arg Ser Gln Val Tyr
420 425 430

Ser Val Ala Ile Val Tyr Gly Phe Leu Val Leu Leu Ser Phe Val Thr
435 440 445

Val Asn Ser Pro Leu Arg Gly Gly Arg Thr Pro Ser Asp Leu Asn
450 455 460

<210> SEQ ID NO 4
<211> LENGTH: 36
<212> TYPE: DNA
<213> ORGANISM: Artificial Sequence
<220> FEATURE:
<223> OTHER INFORMATION: primer

<400> SEQUENCE: 4
aattcgagct cggtaccctt ccccctggag tccgca 36

<210> SEQ ID NO 5
<211> LENGTH: 42
<212> TYPE: DNA
<213> ORGANISM: Artificial Sequence
<220> FEATURE:
<223> OTHER INFORMATION: primer

<400> SEQUENCE: 5
ataggctcgg tcgtttttag gcttgtatca accgtaaacc ca 42

<210> SEQ ID NO 6
<211> LENGTH: 42
<212> TYPE: DNA
<213> ORGANISM: Artificial Sequence
<220> FEATURE:
<223> OTHER INFORMATION: primer

<400> SEQUENCE: 6
tgggtttacg gttgatacaa gcctaaaaac gaccgagcct at 42

<210> SEQ ID NO 7
<211> LENGTH: 40
<212> TYPE: DNA
<213> ORGANISM: Artificial Sequence
<220> FEATURE:
<223> OTHER INFORMATION: primer

<400> SEQUENCE: 7
ccttcattag atttagccat gtgtctcctc taaagattgt 40

<210> SEQ ID NO 8
<211> LENGTH: 40
<212> TYPE: DNA
<213> ORGANISM: Artificial Sequence
<220> FEATURE:
<223> OTHER INFORMATION: primer

<400> SEQUENCE: 8
acaatcttta gaggagacac atggctaaat ctaatgaagg 40

<210> SEQ ID NO 9
<211> LENGTH: 45
<212> TYPE: DNA
<213> ORGANISM: Artificial Sequence
<220> FEATURE:
<223> OTHER INFORMATION: primer

<400> SEQUENCE: 9
gtcgactcta gaggatcccc tcagttcaag tcggaagggg tgcga 45

<210> SEQ ID NO 10
<211> LENGTH: 1338
<212> TYPE: DNA
<213> ORGANISM: Unknown
<220> FEATURE:
<223> OTHER INFORMATION: hom

<400> SEQUENCE: 10
atgacctcag catctgcccc aagctttaac cccggcaagg gtcccggctc agcagtcgga 60
attgcccttt taggattcgg aacagtcggc actgaggtga tgcgtctgat gaccgagtac 120
ggtgatgaac ttgcgcaccg cattggtggc ccactggagg ttcgtggcat tgctgtttct 180
gatatctcaa agccacgtga aggcgttgca cctgagctgc tcactgagga cgcttttgca 240
ctcatcgagc gcgaggatgt tgacatcgtc gttgaggtta tcggcggcat tgagtaccca 300
cgtgaggtag ttctcgcagc tctgaaggcc ggcaagtctg ttgttaccgc caataaggct 360
cttgttgcag ctcactctgc tgagcttgct gatgcagcgg aagccgcaaa cgttgacctg 420
tacttcgagg ctgctgttgc aggcgcaatt ccagtggttg gcccactgcg tcgctccctg 480
gctggcgatc agatccagtc tgtgatgggc atcgttaacg gcaccaccaa cttcatcttg 540
gacgccatgg attccaccgg cgctgactat gcagattctt tggctgaggc aactcgtttg 600
ggttacgccg aagctgatcc aactgcagac gtcgaaggcc atgacgccgc atccaaggct 660
gcaattttgg catccatcgc tttccacacc cgtgttaccg cggatgatgt gtactgcgaa 720
ggtatcagca acatcagcgc tgccgacatt gaggcagcac agcaggcagg ccacaccatc 780
aagttgttgg ccatctgtga gaagttcacc aacaaggaag gaaagtcggc tatttctgct 840
cgcgtgcacc cgactctatt acctgtgtcc cacccactgg cgtcggtaaa caagtccttt 900
aatgcaatct ttgttgaagc agaagcagct ggtcgcctga tgttctacgg aaacggtgca 960
ggtggcgcgc caaccgcgtc tgctgtgctt ggcgacgtcg ttggtgccgc acgaaacaag 1020
gtgcacggtg gccgtgctcc aggtgagtcc acctacgcta acctgccgat cgctgatttc 1080
ggtgagacca ccactcgtta ccacctcgac atggatgtgg aagatcgcgt gggggttttg 1140
gctgaattgg ctagcctgtt ctctgagcaa ggaatctccc tgcgtacaat ccgacaggaa 1200
gagcgcgatg atgatgcaca tctgatcgtg gtcacccact ctgcgctgga atctgatctt 1260
tcccgcaccg ttgaactgct gaaggctaag cctgttgtta aggcaatcaa cagtgtgatc 1320
cgcctcgaaa gggactaa 1338

<210> SEQ ID NO 11
<211> LENGTH: 35
<212> TYPE: DNA
<213> ORGANISM: Artificial Sequence
<220> FEATURE:
<223> OTHER INFORMATION: primer

<400> SEQUENCE: 11
tcgagctcgg taccccgctt ttgcactcat cgagc 35

<210> SEQ ID NO 12
<211> LENGTH: 23
<212> TYPE: DNA
<213> ORGANISM: Artificial Sequence
<220> FEATURE:
<223> OTHER INFORMATION: primer

<400> SEQUENCE: 12
cacgatcaga tgtgcatcat cat 23

<210> SEQ ID NO 13
<211> LENGTH: 23
<212> TYPE: DNA
<213> ORGANISM: Artificial Sequence
<220> FEATURE:
<223> OTHER INFORMATION: primer

<400> SEQUENCE: 13
atgatgatgc acatctgatc gtg 23

<210> SEQ ID NO 14
<211> LENGTH: 35
<212> TYPE: DNA
<213> ORGANISM: Artificial Sequence
<220> FEATURE:
<223> OTHER INFORMATION: primer

<400> SEQUENCE: 14
ctctagagga tccccgagca tcttccaaaa ccttg 35

<210> SEQ ID NO 15
<211> LENGTH: 1311
<212> TYPE: DNA
<213> ORGANISM: Unknown
<220> FEATURE:
<223> OTHER INFORMATION: ilvA

<400> SEQUENCE: 15
atgagtgaaa catacgtgtc tgagaaaagt ccaggagtga tggctagcgg agcggagctg 60
attcgtgccg ccgacattca aacggcgcag gcacgaattt cctccgtcat tgcaccaact 120
ccattgcagt attgccctcg tctttctgag gaaaccggag cggaaatcta ccttaagcgt 180
gaggatctgc aggatgttcg ttcctacaag atccgcggtg cgctgaactc tggagcgcag 240
ctcactcagg agcagcgcga tgcaggtatc gttgccgcat ctgcaggtaa ccatgcccag 300
ggcgtggcct atgtgtgcaa gtccttgggc gttcagggac gcatctatgt tcctgtgcag 360
actccaaagc aaaagcgtga ccgcatcatg gttcacggcg gagagtttgt ctccttggtg 420
gtcactggca ataacttcga cgaagcatcg gctgcagcgc atgaagatgc agagcgcacc 480
ggcgcaacgc tgatcgagcc tttcgatgct cgcaacaccg tcatcggtca gggtacagtg 540
gctgctgaga tcttgtcgca gctgacttcc atgggcaaga gtgcagatca cgtgatggtt 600
ccagtcggcg gtggcggact tcttgcaggt gtggtcagct acatggctga tatggcacct 660
cgcactgcga tcgttggtat cgaaccagcg ggagcagcat ccatgcaggc tgcattgcac 720
aatggtggac caatcacttt ggagactgtt gatccctttg tggacggcgc agcagtcaaa 780
cgtgtcggag atctcaacta caccatcgtg gagaagaacc agggtcgcgt gcacatgatg 840
agcgcgaccg agggcgctgt gtgtactgag atgctcgatc tttaccaaaa cgaaggcatc 900
atcgcggagc ctgctggcgc gctgtctatc gctgggttga aggaaatgtc ctttgcacct 960
ggttctgtcg tggtgtgcat catctctggt ggcaacaacg atgtgctgcg ttatgcggaa 1020
atcgctgagc gctccttggt gcaccgcggt ttgaagcact acttcttggt gaacttcccg 1080
caaaagcctg gtcagttgcg tcacttcctg gaagatatcc tgggaccgga tgatgacatc 1140
gcgctggcag agtacctcaa gcgcaacaac cgtgagaccg gtactgcgtt ggtgggtatt 1200
cacttgagtg aagcatcagg attggattct ttgctggaac gtatggagga atcggcaatt 1260
gattcccgtc gcctcgagcc gggcacccct gagtacgaat acttgaccta a 1311

<210> SEQ ID NO 16
<211> LENGTH: 35
<212> TYPE: DNA
<213> ORGANISM: Artificial Sequence
<220> FEATURE:
<223> OTHER INFORMATION: primer

<400> SEQUENCE: 16
tcgagctcgg tacccatgag tgaaacatac gtgtc 35

<210> SEQ ID NO 17

<211> LENGTH: 39
<212> TYPE: DNA
<213> ORGANISM: Artificial Sequence
<220> FEATURE:
<223> OTHER INFORMATION: primer

<400> SEQUENCE: 17
gcgcttgagg tactctgcca gcgcgatgtc atcatccgg 39

<210> SEQ ID NO 18
<211> LENGTH: 39
<212> TYPE: DNA
<213> ORGANISM: Artificial Sequence
<220> FEATURE:
<223> OTHER INFORMATION: primer

<400> SEQUENCE: 18
ccggatgatg acatcgcgct ggcagagtac ctcaagcgc 39

<210> SEQ ID NO 19
<211> LENGTH: 34
<212> TYPE: DNA
<213> ORGANISM: Artificial Sequence
<220> FEATURE:
<223> OTHER INFORMATION: primer

<400> SEQUENCE: 19
ctctagagga tcccccgtca ccgacacctc caca 34

<210> SEQ ID NO 20
<211> LENGTH: 463
<212> TYPE: PRT
<213> ORGANISM: Unknown
<220> FEATURE:
<223> OTHER INFORMATION: aroP

<400> SEQUENCE: 20

```
Met Ala Lys Ser Asn Glu Gly Leu Gly Thr Gly Leu Arg Thr Arg His
1               5                   10                  15

Leu Thr Met Met Gly Leu Gly Ser Ala Ile Gly Ala Gly Leu Phe Leu
            20                  25                  30

Gly Thr Gly Val Gly Ile Arg Ala Ala Gly Pro Ala Val Leu Leu Ala
        35                  40                  45

Tyr Ile Ile Ala Gly Ala Ile Val Val Leu Val Met Gln Met Leu Gly
    50                  55                  60

Glu Met Ala Ala Ala Arg Pro Ala Ser Gly Ser Phe Ser Arg Tyr Gly
65                  70                  75                  80

Glu Asp Ala Phe Gly His Trp Ala Gly Phe Ser Leu Gly Trp Leu Tyr
                85                  90                  95

Trp Phe Met Leu Ile Met Val Met Gly Ala Glu Met Thr Gly Ala Ala
            100                 105                 110

Ala Phe Met Gly Ala Trp Phe Gly Val Glu Pro Trp Ile Pro Ser Leu
        115                 120                 125

Val Cys Val Val Phe Phe Ala Val Val Asn Leu Val Ala Val Arg Gly
    130                 135                 140

Phe Gly Glu Phe Glu Tyr Trp Phe Ala Phe Ile Lys Val Ala Val Ile
145                 150                 155                 160

Ile Ala Phe Leu Ile Ile Gly Ile Ala Leu Ile Phe Gly Trp Leu Pro
                165                 170                 175

Gly Ser Thr Phe Val Gly Thr Ser Asn Phe Ile Gly Asp His Gly Phe
            180                 185                 190
```

Met Pro Asn Gly Ile Ser Gly Val Ala Ala Gly Leu Leu Ala Val Ala
195 200 205

Phe Ala Phe Gly Gly Ile Glu Ile Val Thr Ile Ala Ala Ala Glu Ser
210 215 220

Asp Lys Pro Arg Glu Ala Ile Ser Leu Ala Val Arg Ala Val Ile Trp
225 230 235 240

Arg Ile Ser Val Phe Tyr Leu Gly Ser Val Leu Val Ile Thr Phe Leu
245 250 255

Met Pro Tyr Glu Ser Ile Asn Gly Ala Asp Thr Ala Ala Glu Ser Pro
260 265 270

Phe Thr Gln Ile Leu Ala Met Ala Asn Ile Pro Gly Thr Val Gly Phe
275 280 285

Met Glu Ala Ile Ile Val Leu Ala Leu Leu Ser Ala Phe Asn Ala Gln
290 295 300

Ile Tyr Ala Thr Ser Arg Leu Val Phe Ser Met Ala Asn Arg Gln Asp
305 310 315 320

Ala Pro Arg Val Phe Ser Lys Leu Ser Thr Ser His Val Pro Thr Asn
325 330 335

Ala Val Leu Leu Ser Met Phe Phe Ala Phe Val Ser Val Gly Leu Gln
340 345 350

Tyr Trp Asn Pro Ala Gly Leu Leu Asp Phe Leu Leu Asn Ala Val Gly
355 360 365

Gly Cys Leu Ile Val Val Trp Ala Met Ile Thr Leu Ser Gln Leu Lys
370 375 380

Leu Arg Lys Glu Leu Gln Ala Asn Asp Glu Ile Ser Thr Val Arg Met
385 390 395 400

Trp Ala His Pro Trp Leu Gly Ile Leu Thr Leu Val Leu Leu Ala Gly
405 410 415

Leu Val Ala Leu Met Leu Gly Asp Ala Ala Ser Arg Ser Gln Val Tyr
420 425 430

Ser Val Ala Ile Val Tyr Gly Phe Leu Val Leu Leu Ser Phe Val Thr
435 440 445

Val Asn Ser Pro Leu Arg Gly Gly Arg Thr Pro Ser Asp Leu Asn
450 455 460

<210> SEQ ID NO 21
<211> LENGTH: 463
<212> TYPE: PRT
<213> ORGANISM: Unknown
<220> FEATURE:
<223> OTHER INFORMATION: aroP

<400> SEQUENCE: 21

Met Ala Lys Ser Asn Glu Gly Leu Gly Thr Gly Leu Arg Thr Arg His
1 5 10 15

Leu Thr Met Met Gly Leu Gly Ser Ala Ile Gly Val Gly Leu Phe Leu
20 25 30

Gly Thr Gly Val Gly Ile Arg Ala Ala Gly Pro Ala Val Leu Leu Ala
35 40 45

Tyr Ile Ile Ala Gly Ala Ile Val Val Leu Val Met Gln Met Leu Gly
50 55 60

Glu Met Ala Ala Ala Arg Pro Ala Ser Gly Ser Phe Ser Arg Tyr Gly
65 70 75 80

Glu Asp Ala Phe Gly His Trp Ala Gly Phe Ser Leu Gly Trp Leu Tyr
85 90 95

```
Trp Phe Met Leu Ile Met Val Met Gly Ala Glu Met Thr Gly Ala Ala
            100                 105                 110

Ala Ile Met Gly Ala Trp Phe Gly Val Glu Pro Trp Ile Pro Ser Leu
        115                 120                 125

Val Cys Val Val Phe Phe Ala Val Val Asn Leu Val Ala Val Arg Gly
    130                 135                 140

Phe Gly Glu Phe Glu Tyr Trp Phe Ala Phe Ile Lys Val Ala Val Ile
145                 150                 155                 160

Ile Ala Phe Leu Ile Ile Gly Ile Ala Leu Ile Phe Gly Trp Leu Pro
                165                 170                 175

Gly Ser Thr Phe Val Gly Thr Ser Asn Phe Ile Gly Asp His Gly Phe
            180                 185                 190

Met Pro Asn Gly Ile Ser Gly Val Ala Ala Gly Leu Leu Ala Val Ala
        195                 200                 205

Phe Ala Phe Gly Gly Ile Glu Ile Val Thr Ile Ala Ala Ala Glu Ser
    210                 215                 220

Asp Lys Pro Arg Glu Ala Ile Ser Leu Ala Val Arg Ala Val Ile Trp
225                 230                 235                 240

Arg Ile Ser Val Phe Tyr Leu Gly Ser Val Leu Val Ile Thr Phe Leu
                245                 250                 255

Met Pro Tyr Glu Ser Ile Asn Gly Ala Asp Thr Ala Ala Glu Ser Pro
            260                 265                 270

Phe Thr Gln Ile Leu Ala Met Ala Asn Ile Pro Gly Thr Val Gly Phe
        275                 280                 285

Met Glu Ala Ile Ile Val Leu Ala Leu Leu Ser Ala Phe Asn Ala Gln
    290                 295                 300

Ile Tyr Ala Thr Ser Arg Leu Val Phe Ser Met Ala Asn Arg Gln Asp
305                 310                 315                 320

Ala Pro Arg Val Phe Ser Lys Leu Ser Thr Ser His Val Pro Thr Asn
                325                 330                 335

Ala Val Leu Leu Ser Met Phe Phe Ala Phe Val Ser Val Gly Leu Gln
            340                 345                 350

Tyr Trp Asn Pro Ala Gly Leu Leu Asp Phe Leu Leu Asn Ala Val Gly
        355                 360                 365

Gly Cys Leu Ile Val Val Trp Ala Met Ile Thr Leu Ser Gln Leu Lys
    370                 375                 380

Leu Arg Lys Glu Leu Gln Ala Asn Asp Glu Ile Ser Thr Val Arg Met
385                 390                 395                 400

Trp Ala His Pro Trp Leu Gly Ile Leu Thr Leu Val Leu Leu Ala Gly
                405                 410                 415

Leu Val Ala Leu Met Leu Gly Asp Ala Ala Ser Arg Ser Gln Val Tyr
            420                 425                 430

Ser Val Ala Ile Val Tyr Gly Phe Leu Val Leu Leu Ser Phe Val Thr
        435                 440                 445

Val Asn Ser Pro Leu Arg Gly Gly Arg Thr Pro Ser Asp Leu Asn
    450                 455                 460
```

<210> SEQ ID NO 22
<211> LENGTH: 1392
<212> TYPE: DNA
<213> ORGANISM: Unknown
<220> FEATURE:
<223> OTHER INFORMATION: aroP

<400> SEQUENCE: 22

```
atggctaaat ctaatgaagg gctgggaacc ggacttcgga cccgccacct cacaatgatg      60
ggactcggct ccgcaattgg tgccggactg ttcctcggca ccggcgttgg tatccgcgca     120
gccggccccg cagtgctcct ggcgtacatc atcgccggag ccatcgttgt gcttgttatg     180
caaatgctcg gcgagatggc tgctgcccgt cccgcctccg gatcgttttc acgttacggc     240
gaggatgctt tcggccactg ggctggtttc tccctcggtt ggttgtactg gttcatgctg     300
attatggtga tgggcgccga aatgactggc gctgctgcca tcatgggtgc atggttcggc     360
gtcgaaccgt ggattccttc gcttgtctgc gtggtcttct tcgctgtggt gaacctcgtc     420
gcggttcgcg gtttcggtga attcgagtac tggttcgcat tcattaaggt cgcggtgatc     480
atcgctttcc tcatcattgg tattgctctt attttcggat ggcttcccgg atccaccttt     540
gttggaacct caaacttcat cggtgatcac ggattcatgc ccaatggtat ttctggtgtt     600
gctgctggtt tgctcgcggt ggcttttgcc tttaccggca ttgaaattgt caccattgca     660
gctgcagagt ccgataagcc acgtgaagct atttccctgg cggtgcgtgc cgtgatttgg     720
cgtatttcag tcttttactt gggctctgtt ttggtcatca ctttcctcat gccttatgag     780
tcgatcaatg gtgccgacac cgctgcggaa tccccccttca cccaaatcct ggcgatggca     840
aacatccctg gcacggttgg tttcatggaa gcgatcatcg ttctagcact gctttccgct     900
ttcaacgccc aaatctatgc cacttctcgt ttggtatttt ccatggcgaa tcgacaagac     960
gctccgcgag ttttcagtaa gctcagcacc agccacgtcc ccaccaatgc ggtgctgttg    1020
tccatgttct tcgccttcgt ttcagttggt ttgcagtact ggaatccagc cggtctgctt    1080
gatttcctcc tcaacgctgt tggcggttgt ttgattgtgg tgtgggcaat gatcactttg    1140
tcacagttga aactccgcaa agaactgcaa gcaaacgatg aaatctccac ggttcgcatg    1200
tgggcgcacc catggttagg catcctcacc ttggttttgt tggcaggact cgttgctctc    1260
atgctcggcg acgcagcctc ccgcagccag gtttactcag tggcaattgt gtacggattc    1320
ttggttcttt tgtccttcgt cacagttaac agcccattgc gcggaggtcg caccccttcc    1380
gacttgaact ga                                                         1392
```

<210> SEQ ID NO 23
<211> LENGTH: 1392
<212> TYPE: DNA
<213> ORGANISM: Unknown
<220> FEATURE:
<223> OTHER INFORMATION: aroP

<400> SEQUENCE: 23

```
atggctaaat ctaatgaagg gctgggaacc ggacttcgga cccgccacct cacaatgatg      60
ggactcggct ccgcaattgg tgccggactg ttcctcggca ccggcgttgg tatccgcgca     120
gccggccccg cagtgctcct ggcgtacatc atcgccggag ccatcgttgt gcttgttatg     180
caaatgctcg gcgagatggc tgctgcccgt cccgcctccg gatcgttttc acgttacggc     240
gaggatgctt tcggccactg ggctggtttc tccctcggtt ggttgtactg gttcatgctg     300
attatggtga tgggcgccga aatgactggc gctgctgcct tcatgggtgc atggttcggc     360
gtcgaaccgt ggattccttc gcttgtctgc gtggtcttct tcgctgtggt gaacctcgtc     420
gcggttcgcg gtttcggtga attcgagtac tggttcgcat tcattaaggt cgcggtgatc     480
atcgctttcc tcatcattgg tattgctctt attttcggat ggcttcccgg atccaccttt     540
gttggaacct caaacttcat cggtgatcac ggattcatgc ccaatggtat ttctggtgtt     600
```

gctgctggtt tgctcgcggt ggcttttgcc tttggtggca ttgaaattgt caccattgca 660
gctgcagagt ccgataagcc acgtgaagct atttccctgg cggtgcgtgc cgtgatttgg 720
cgtatttcag tcttttactt gggctctgtt ttggtcatca ctttcctcat gccttatgag 780
tcgatcaatg gtgccgacac cgctgcggaa tccccccttca cccaaatcct ggcgatggca 840
aacatccctg gcacggttgg tttcatggaa gcgatcatcg ttctagcact gctttccgct 900
ttcaacgccc aaatctatgc cacttctcgt ttggtatttt ccatggcgaa tcgacaagac 960
gctccgcgag ttttcagtaa gctcagcacc agccacgtcc ccaccaatgc ggtgctgttg 1020
tccatgttct tcgccttcgt ttcagttggt ttgcagtact ggaatccagc cggtctgctt 1080
gatttcctcc tcaacgctgt tggcggttgt ttgattgtgg tgtgggcaat gatcactttg 1140
tcacagttga aactccgcaa agaactgcaa gcaaacgatg aaatctccac ggttcgcatg 1200
tgggcgcacc catggttagg catcctcacc ttggttttgt tggcaggact cgttgctctc 1260
atgctcggcg acgcagcctc ccgcagccag gtttactcag tggcaattgt gtacggattc 1320
ttggttcttt tgtccttcgt cacagttaac agcccattgc gcggaggtcg cacccccttcc 1380
gacttgaact ga 1392

<210> SEQ ID NO 24
<211> LENGTH: 1392
<212> TYPE: DNA
<213> ORGANISM: Unknown
<220> FEATURE:
<223> OTHER INFORMATION: aroP

<400> SEQUENCE: 24
atggctaaat ctaatgaagg gctgggaacc ggacttcgga cccgccacct cacaatgatg 60
ggactcggct ccgcaattgg tgttggactg ttcctcggca ccggcgttgg tatccgcgca 120
gccggccccg cagtgctcct ggcgtacatc atcgccggag ccatcgttgt gcttgttatg 180
caaatgctcg gcgagatggc tgctgcccgt cccgcctccg gatcgttttc acgttacggc 240
gaggatgctt tcggccactg ggctggtttc tccctcggtt ggttgtactg gttcatgctg 300
attatggtga tgggcgccga aatgactggc gctgctgcca tcatgggtgc atggttcggc 360
gtcgaaccgt ggattccttc gcttgtctgc gtggtcttct tcgctgtggt gaacctcgtc 420
gcggttcgcg gtttcggtga attcgagtac tggttcgcat tcattaaggt cgcggtgatc 480
atcgctttcc tcatcattgg tattgctctt attttcggat ggcttcccgg atccaccttt 540
gttggaacct caaacttcat cggtgatcac ggattcatgc ccaatggtat ttctggtgtt 600
gctgctggtt tgctcgcggt ggcttttgcc tttggtggca ttgaaattgt caccattgca 660
gctgcagagt ccgataagcc acgtgaagct atttccctgg cggtgcgtgc cgtgatttgg 720
cgtatttcag tcttttactt gggctctgtt ttggtcatca ctttcctcat gccttatgag 780
tcgatcaatg gtgccgacac cgctgcggaa tccccccttca cccaaatcct ggcgatggca 840
aacatccctg gcacggttgg tttcatggaa gcgatcatcg ttctagcact gctttccgct 900
ttcaacgccc aaatctatgc cacttctcgt ttggtatttt ccatggcgaa tcgacaagac 960
gctccgcgag ttttcagtaa gctcagcacc agccacgtcc ccaccaatgc ggtgctgttg 1020
tccatgttct tcgccttcgt ttcagttggt ttgcagtact ggaatccagc cggtctgctt 1080
gatttcctcc tcaacgctgt tggcggttgt ttgattgtgg tgtgggcaat gatcactttg 1140
tcacagttga aactccgcaa agaactgcaa gcaaacgatg aaatctccac ggttcgcatg 1200
tgggcgcacc catggttagg catcctcacc ttggttttgt tggcaggact cgttgctctc 1260
atgctcggcg acgcagcctc ccgcagccag gtttactcag tggcaattgt gtacggattc 1320
ttggttcttt tgtccttcgt cacagttaac agcccattgc gcggaggtcg caccccttcc 1380
gacttgaact ga 1392

<210> SEQ ID NO 25
<211> LENGTH: 436
<212> TYPE: PRT
<213> ORGANISM: Unknown
<220> FEATURE:
<223> OTHER INFORMATION: ilvA

<400> SEQUENCE: 25

Met Ser Glu Thr Tyr Val Ser Glu Lys Ser Pro Gly Val Met Ala Ser
1 5 10 15

Gly Ala Glu Leu Ile Arg Ala Ala Asp Ile Gln Thr Ala Gln Ala Arg
20 25 30

Ile Ser Ser Val Ile Ala Pro Thr Pro Leu Gln Tyr Cys Pro Arg Leu
35 40 45

Ser Glu Glu Thr Gly Ala Glu Ile Tyr Leu Lys Arg Glu Asp Leu Gln
50 55 60

Asp Val Arg Ser Tyr Lys Ile Arg Gly Ala Leu Asn Ser Gly Ala Gln
65 70 75 80

Leu Thr Gln Glu Gln Arg Asp Ala Gly Ile Val Ala Ala Ser Ala Gly
85 90 95

Asn His Ala Gln Gly Val Ala Tyr Val Cys Lys Ser Leu Gly Val Gln
100 105 110

Gly Arg Ile Tyr Val Pro Val Gln Thr Pro Lys Gln Lys Arg Asp Arg
115 120 125

Ile Met Val His Gly Gly Glu Phe Val Ser Leu Val Val Thr Gly Asn
130 135 140

Asn Phe Asp Glu Ala Ser Ala Ala Ala His Glu Asp Ala Glu Arg Thr
145 150 155 160

Gly Ala Thr Leu Ile Glu Pro Phe Asp Ala Arg Asn Thr Val Ile Gly
165 170 175

Gln Gly Thr Val Ala Ala Glu Ile Leu Ser Gln Leu Thr Ser Met Gly
180 185 190

Lys Ser Ala Asp His Val Met Val Pro Val Gly Gly Gly Gly Leu Leu
195 200 205

Ala Gly Val Val Ser Tyr Met Ala Asp Met Ala Pro Arg Thr Ala Ile
210 215 220

Val Gly Ile Glu Pro Ala Gly Ala Ala Ser Met Gln Ala Ala Leu His
225 230 235 240

Asn Gly Gly Pro Ile Thr Leu Glu Thr Val Asp Pro Phe Val Asp Gly
245 250 255

Ala Ala Val Lys Arg Val Gly Asp Leu Asn Tyr Thr Ile Val Glu Lys
260 265 270

Asn Gln Gly Arg Val His Met Met Ser Ala Thr Glu Gly Ala Val Cys
275 280 285

Thr Glu Met Leu Asp Leu Tyr Gln Asn Glu Gly Ile Ile Ala Glu Pro
290 295 300

Ala Gly Ala Leu Ser Ile Ala Gly Leu Lys Glu Met Ser Phe Ala Pro
305 310 315 320

Gly Ser Val Val Val Cys Ile Ile Ser Gly Gly Asn Asn Asp Val Leu
325 330 335

-continued

```
Arg Tyr Ala Glu Ile Ala Glu Arg Ser Leu Val His Arg Gly Leu Lys
            340                 345                 350

His Tyr Phe Leu Val Asn Phe Pro Gln Lys Pro Gly Gln Leu Arg His
        355                 360                 365

Phe Leu Glu Asp Ile Leu Gly Pro Asp Asp Asp Ile Thr Leu Phe Glu
    370                 375                 380

Tyr Leu Lys Arg Asn Asn Arg Glu Thr Gly Thr Ala Leu Val Gly Ile
385                 390                 395                 400

His Leu Ser Glu Ala Ser Gly Leu Asp Ser Leu Leu Glu Arg Met Glu
                405                 410                 415

Glu Ser Ala Ile Asp Ser Arg Arg Leu Glu Pro Gly Thr Pro Glu Tyr
            420                 425                 430

Glu Tyr Leu Thr
        435
```

GAMMA-AMINOBUTYRATE PERMEASE VARIANT AND METHOD FOR PRODUCING ISOLEUCINE USING THE SAME

A computer readable text file, entitled "105135-5069-US_Sequence_Listing.txt," created on or about Jun. 26, 2023, with a file size of 34,227 bytes contains the sequence listing for this application and is hereby incorporated by reference in its entirety.

TECHNICAL FIELD

The present application relates to a novel gamma(γ)-aminobutyrate permease variant that decreases the amount of by-products generated during the production of L-isoleucine, a polynucleotide encoding the variant, and a vector comprising the polynucleotide, a microorganism comprising the variant, polynucleotide or vector, and a method for producing L-isoleucine using the microorganism.

BACKGROUND ART

L-Isoleucine is one of the branched-chain amino acids among the total of 20 amino acids, is classified as an essential amino acid, and is used in the fields of animal feed, food additives, and medicine. After metabolism. L-isoleucine has functions such as energy generation, hemoglobin production, blood sugar level control, and muscle building and repair, and is thus increasingly used in the field of animal feed as well as infusion solutions, nutritional supplements, and sports nutritional supplements.

Based on this trend, various microorganisms and variants thereof are used for the production of L-amino acids (U.S. patent Ser. No. 10/113,190), and in this case as well, a large number of by-products other than L-isoleucine are produced, and the by-products are substances that greatly affect the purity of L-isoleucine in the purification step, and therefore, a method for removing the by-products is required. In this regard, the L-isoleucine purification method developed to increase the purity of L-isoleucine has a disadvantage in that a separate additional purification process is required (U.S. Pat. No. 6,072,083), and there is a need to develop a method for increasing the purity of L-isoleucine.

DISCLOSURE

Technical Problem

As a result of earnest efforts to increase the purity of L-isoleucine at the time of production using microorganisms, an aroP gene encoding a γ-aminobutyrate permease that can decrease the amount of by-products such as α-aminobutyrate and L-valine and contribute to the production of L-isoleucine has been identified, and a variation capable of further increasing the purity of L-isoleucine has been obtained.

Technical Solution

An object of the present application is to provide a γ-aminobutyrate permease variant.

Another object of the present application is to provide a polynucleotide encoding the variant.

Another object of the present application is to provide a vector comprising the polynucleotide.

Another object of the present application is to provide a microorganism, comprising any one or more of the variant; a polynucleotide encoding the variant: and a vector comprising the polynucleotide.

Another object of the present application is to provide a method for producing L-isoleucine.

Another object of the present application is to provide a composition for L-isoleucine production.

Another object of the present application is to provide use of the variant, the polynucleotide encoding the variant, the vector comprising the polynucleotide, or the microorganism for the production of L-isoleucine.

Advantageous Effects

The microorganism expressing a γ-aminobutyrate permease variant of the present application can significantly improve the purity of L-isoleucine compared to a strain that does not express the γ-aminobutyrate permease variant, it is thus possible to effectively produce L-isoleucine by using the microorganism. Consequently, the microorganism can be expected to be used in a wide range of industries such as food, feed, and medicine utilizing L-isoleucine.

DETAILED DESCRIPTION OF THE INVENTION

Hereinafter, the contents of the present application will be described in detail as follows. Meanwhile, descriptions and embodiments of an aspect disclosed in the present application may be applied to descriptions and embodiments of other aspects with respect to common matters. Moreover, all combinations of the various elements disclosed in the present application are within the scope of the present application. In addition, it cannot be seen that the scope of the present application is limited by the detailed description described below.

An aspect of the present application provides a γ-aminobutyrate permease variant, in which the amino acid corresponding to the 212th position is substituted with threonine, the amino acid corresponding to the 114th position is substituted with phenylalanine, or the amino acid corresponding to the 28th position is substituted with valine in the amino acid sequence of SEQ ID NO: 1.

In the variant, the 212th amino acid may be substituted with threonine, the 114th amino acid may be substituted with phenylalanine, or the 28th amino acid may be substituted with valine in the amino acid sequence of SEQ ID NO: 1, and specifically, the amino acid corresponding to the 212th position, which is glycine, may be substituted with threonine, the amino acid corresponding to the 114th position, which is isoleucine, may be substituted with phenylalanine, or the amino acid corresponding to the 28th position, which is alanine, may be substituted with valine in the amino acid sequence of SEQ ID NO: 1, but the variant is not limited thereto.

The variant may consist of any one or more sequences selected from the group consisting of SEQ ID NO: 3, SEQ ID NO: 20, and SEQ ID NO: 21, but is not limited thereto.

Specifically, the variant in which the 212th amino acid (i.e., glycine) in the amino acid sequence of SEQ ID NO: 1 is substituted with threonine may consist of SEQ ID NO: 3; the variant in which the 114th amino acid (i.e., isoleucine) in the amino acid sequence of SEQ ID NO: 1 is substituted with phenylalanine may consist of SEQ ID NO: 20; and the variant in which the 28th amino acid (i.e., alanine) in the amino acid sequence of SEQ ID NO: 1 is substituted with valine may consist of SEQ ID NO: 21, respectively, but the variants are not limited thereto.

The variant of the present application may be one, in which the amino acid corresponding to the 212th, the 114th, or the 28th position in γ-aminobutyrate permease having the amino acid sequence of SEQ ID NO: 1 is substituted with a different amino acid, thereby having enhanced γ-aminobutyrate permease activity due to an increase in the uptake of a by-product, but is not limited thereto.

As used herein, the term "L-isoleucine" refers to an L-amino acid having the chemical formula $HO_2CCH(NH_2)CH(CH_3)CH_2CH_3$, which is one of the essential amino acids and structurally corresponds to a branched-chain amino acid together with L-valine and L-leucine.

As used herein, the "γ-aminobutyrate permease" is a polypeptide or protein having γ-aminobutyrate permease activity, and refers to a protein or polypeptide having α-aminobutyrate or L-valine uptake activity. The γ-aminobutyrate permease may be a protein or polypeptide having an uptake activity of L-phenylalanine, L-tyrosine, L-tryptophan, or L-histidine as well as α-aminobutyrate or L-valine, which are by-products generated during the production of L-isoleucine, but is not limited thereto. The γ-aminobutyrate permease may be used interchangeably with aromatic amino-acid permease, and the gene encoding the γ-aminobutyrate permease may be used interchangeably with aroP gene, and γ-aminobutyrate permease may be used interchangeably with AroP.

The γ-aminobutyrate permease may be a protein including the amino acid sequence of SEQ ID NO: 1. The protein including the amino acid sequence of SEQ ID NO: 1 may be used interchangeably with the protein having the amino acid sequence of SEQ ID NO: 1 and the protein consisting of the amino acid sequence of SEQ ID NO: 1.

Specifically, SEQ ID NO: 1 may be the amino acid sequence of γ-aminobutyrate permease encoded by the aroP gene, and the amino acid sequence of SEQ ID NO: 1 may be acquired from various databases such as NCBI GenBank, which is a known database, but is not limited thereto. For example, the amino acid sequence of SEQ ID NO: 1 may be derived from *Corynebacterium* sp., or may be derived from *Corynebacterium glutamicum*, but is not limited thereto, and may include sequences having the same activity as that of the amino acid sequence of SEQ ID NO: 1 without limitation. Additionally, although the protein having γ-aminobutyrate permease activity in the present application has been described as a polypeptide or protein including the amino acid of SEQ ID NO: 1, addition of meaningless sequences before and after the amino acid sequence of SEQ ID NO: 1 or mutations that may occur naturally or silent mutations thereof are not excluded, and it may be apparent to those skilled in the art that a protein having activity the same as or corresponding to that of the protein including the amino acid sequence of SEQ ID NO: 1 corresponds to the polypeptide or protein having aminobutyrate permease activity of the present application. As a specific example, the polypeptide having aminobutyrate permease activity of the present application may be a polypeptide consisting of the amino acid sequence of SEQ ID NO: 1 or an amino acid sequence having 80%, 85%, 90%, 95%, 96%, 97%, 98%, or 99% or more homology or identity thereto. It may be apparent that a polypeptide having an amino acid sequence in which some sequences are deleted, modified, substituted, or added is also included within the range of the polypeptide of the present application as long as the amino acid sequence has such homology or identity and exhibits efficacy corresponding to that of the polypeptide.

In the present application, although it is described as a 'polypeptide or protein including an amino acid sequence of a specific SEQ ID NO:', a 'polypeptide or protein consisting of an amino acid sequence of a specific SEQ ID NO:' or a 'polypeptide or protein having an amino acid sequence of a specific SEQ ID NO:', it is apparent that a protein having an amino acid sequence in which some sequences are deleted, modified, substituted, conservatively substituted or added may also be used in the present application as long as it has activity the same as or corresponding to that of the polypeptide consisting of the amino acid sequence of the corresponding SEQ ID NO. Examples thereof include a case where the amino acid sequence N-terminus and/or C-terminus may have a sequence addition that does not alter the function of the protein, a naturally occurring mutation, a silent mutation thereof, or a conservative substitution.

In the present application, as the method for securing the aminobutyrate permease, various methods well known in the art are applicable. As an example of the method, it is possible to secure a mutant strain using a for screening method useful enzyme resources by a gene synthesis technology including codon optimization and a bioinformatic method based on a large amount of genomic information of microorganisms so as to secure enzymes from microorganisms commonly and widely used for enzyme expression with high efficiency, but the method is not limited thereto.

As used herein, the term "variation" or "variant" refers to a culture or individual that genetically or non-genetically exhibits one stable phenotypic change, and specifically, in the present application, this may be a variant in which the amino acid of aminobutyrate permease having the amino acid sequence of SEQ ID NO: 1 is mutated and the activity thereof is efficiently increased compared to that of the wild-type, but is not limited thereto.

As used herein, the term "variant" or "modified polypeptide" refers to a protein in which one or more amino acids differ from the recited sequence in conservative substitutions and/or modifications but the functions or properties of the protein are maintained. The variant differs from the identified sequence by several amino acid substitutions, deletions or additions. Such a variant may generally be identified by modifying one or more amino acids in the amino acid sequence of the protein and evaluating the properties of the modified protein. In other words, the ability of the variant may be increased, unchanged, or decreased compared to that of the native protein. Additionally, some variants may include modified polypeptides in which one or more portions, such as an N-terminal leader sequence or a transmembrane domain, have been removed. Other variants may include variants in which a portion is removed from the N- and/or C-terminus of the mature protein. The term "variant" or "modified polypeptide" may be used interchangeably with terms such as modification, modified protein, mutant, mutein, divergent, and variant, but is not limited thereto as long as it is a term used in a mutated sense.

For the purposes of the present application, the variant may be a modified protein having increased activity compared to that of the natural wild-type or unmodified protein, but is not limited thereto.

As used herein, the term "conservative substitution" refers to substituting one amino acid with another amino acid having similar structural and/or chemical properties. The variant may have, for example, one or more conservative substitutions while still maintaining one or more biological activities. Such amino acid substitutions may generally occur based on similarity in polarity, charge, solubility, hydrophobicity, hydrophilicity and/or amphipathic nature of the residues.

For example, amino acids with side chains may be classified into positively charged (basic) amino acids among amino acids with electrically charged side chains including arginine, lysine, and histidine and negatively charged (acidic) amino acids including glutamic acid and aspartic acid; and amino acids with uncharged side chains including glycine, alanine, valine, leucine, isoleucine, methionine, phenylalanine, tryptophan, proline, serine, threonine, cysteine, tyrosine, asparagine, and glutamine.

The variant may include deletions or additions of amino acids that have minimal effect on the secondary structure and properties of the polypeptide. For example, the polypeptide may be conjugated with a signal (or leader) sequence at the N-terminus of the protein, which is involved in the transfer of the protein either co-translationally or post-translationally. The polypeptide may be conjugated with other sequences or linkers so that identification, purification, or synthesis of the polypeptide is possible.

The variant of the present application may have γ-aminobutyrate permease activity, and may have increased γ-aminobutyrate permease activity, but is not limited thereto.

The variant having γ-aminobutyrate permease activity of the present application is described as a polypeptide or protein in which the amino acid corresponding to the 212th position is substituted with threonine, the amino acid corresponding to the 114th position is substituted with phenylalanine, or the amino acid corresponding to the 28th position is substituted with valine in the amino acid sequence of SEQ ID NO: 1, but does not exclude the addition of meaningless sequences before or after the amino acid sequence, in which the amino acid corresponding to the 212th position is substituted with threonine, the amino acid corresponding to the 114th position is substituted with phenylalanine, or the amino acid corresponding to the 28th position is substituted with valine in the amino acid sequence of SEQ ID NO: 1, or mutations that may occur naturally, or silent mutations thereof, and it may be apparent to those skilled in the art that a protein having activity the same as or corresponding to that of the protein including the amino acid sequence, in which the amino acid corresponding to the 212th position is substituted with threonine, the amino acid corresponding to the 114th position is substituted with phenylalanine, or the amino acid corresponding to the 28th position is substituted with valine in the amino acid sequence of SEQ ID NO: 1, corresponds to the polypeptide, protein, or variant having γ-aminobutyrate permease activity of the present application. As a specific example, the polypeptide or variant having γ-aminobutyrate permease activity of the present application may be a polypeptide consisting of an amino acid sequence, in which the amino acid corresponding to the 212th position is substituted with threonine, the amino acid corresponding to the 114th position is substituted with phenylalanine, or the amino acid corresponding to the 28th position is substituted with valine in the amino acid sequence of SEQ ID NO: 1, or an amino acid sequence having 80%, 85%, 90%, 95%, 96%, 97%, 98%, or 99% or more homology or identity thereto. It may be apparent that a polypeptide having an amino acid sequence in which some sequences are deleted, modified, substituted, or added is also included within the range of the polypeptide of the present application as long as the amino acid sequence has such homology or identity and exhibits efficacy corresponding to that of the polypeptide.

As used herein, the term "corresponding" or "corresponding position" refers to an amino acid residue at a position recited in a protein or polypeptide, or an amino acid residue that is similar to, identical to, or homologous to a residue recited in a protein or polypeptide. As used herein, the term "corresponding region" generally refers to a similar or corresponding location in a related protein or reference protein.

In the present application, specific numbering may be used for amino acid residue positions in the protein used in the present application. For example, it is possible to renumber the location corresponding to the amino acid residue location in the protein of the present application by aligning the polypeptide sequences of the protein of the present application and the target protein to be compared.

As used herein, the term "homology" or "identity" refers to the degree of relation between two given amino acid sequences or nucleotide sequences and may be expressed as a percentage. The terms homology and identity may often be used interchangeably.

The sequence homology or identity of a conserved polynucleotide or polypeptide is determined by a standard alignment algorithm, and a default gap penalty established by the program being used may be used together. Substantially homologous or identical sequences are generally capable of hybridizing under moderate or high stringent conditions along the full sequence or at least about 50%, 60%, 70%, 80%, or 90% of the full-length sequence. It is apparent that hybridization also includes polynucleotides containing common codons in polynucleotides or codons taking codon degeneracy into account.

Whether arbitrary two polynucleotide or polypeptide sequences have homology, similarity, or identity may be determined, for example, using default parameters as in Pearson et al. (1988) *Proc. Natl. Acad. Sci. USA* 85:2444 and known computer algorithms such as the "FASTA" program. Alternatively, the Needleman-Wunsch algorithm (Needleman and Wunsch, 1970, *J. Mol. Biol* 48:443-453) as performed in the Needleman program of the EMBOSS package (EMBOSS: The European Molecular Biology Open Software Suite, Rice et al., 2000, *Trends Genet* 16:276-277) (version 5.0.0 or later) may be used to determine the homology, similarity, or identity (including GCG program package (Devereux, J., et al., *Nucleic Acids Research* 12:387 (1984)), BLASTP, BLASTN, FASTA (Atschul, S. F., et al., *J MOLEC BIOL* 215:403 (1990); *Guide to Huge Computers*, Martin J. Bishop, Ed., Academic Press, San Diego, 1994, and CARILLO et al. (1988) *SIAM J Applied Math* 48:1073). For example, BLAST from the National Center for Biotechnology Information, or ClustalW may be used to determine the homology, similarity, or identity.

The homology, similarity, or identity of polynucleotides or polypeptides may be determined by comparing the sequence information, for example, using a GAP computer program such as Needleman et al. (1970), *J Mol Biol.* 48:443, for example, as known in Smith and Waterman, *Adv. Appl. Math* (1981) 2:482. In summary, the homology, similarity, or identity may be defined as the value acquired by dividing the number of similarly arranged symbols (namely, nucleotides or amino acids) by the total number of symbols in the shorter of the two sequences in a GAP program. Default parameters for the GAP program may include (1) binary comparison matrix (containing values of 1 for identity and 0 for non-identity) and weighted comparison matrix of Gribskov et al. (1986) *Nucl. Acids Res.* 14:6745 (or EDNAFULL (EMBOSS version of NCBI NUC4.4) substitution matrix) as disclosed by Schwartz and Dayhoff, eds.,

*Atlas Of Protein Sequence And Structure*, National Biomedical Research Foundation, pp. 353-358 (1979); (2) a penalty of 3.0 for each gap and an additional penalty of 0.10 for each symbol in each gap (or a gap opening penalty of 10, a gap extension penalty of 0.5); and (3) no penalty for an end gap.

Whether arbitrary two polynucleotide or polypeptide sequences have homology, similarity, or identity may be confirmed by comparing the sequences through Southern hybridization experiments under defined stringent conditions, and appropriate hybridization conditions to be defined are within the scope of the art, and may be determined by way of methods (for example, J. Sambrook et al., *Molecular Cloning, A Laboratory Manual,* 2nd Edition, Cold Spring Harbor Laboratory press, Cold Spring Harbor, New York, 1989; F. M. Ausubel et at, *Current Protocols in Molecular Biology*, John Wiley & Sons, Inc., New York) well known to those skilled in the art.

Another aspect of the present application provides a polynucleotide encoding the γ-aminobutyrate permease variant of the present application. Specifically, there is provided a polynucleotide encoding a γ-aminobutyrate permease variant in which the amino acid corresponding to the 212th position is substituted with threonine, the amino acid corresponding to the 114th position is substituted with phenylalanine, or the amino acid corresponding to the 28th position is substituted with valine in the amino acid sequence of SEQ ID NO: 1.

The amino acid sequence of SEQ ID NO: 1, γ-aminobutyrate permease, and variant are as described above.

In the present application, the amino acid sequence of SEQ ID NO: 1 may be, for example, encoded by a polynucleotide including the nucleic acid sequence of SEQ ID NO: 2, and the γ-aminobutyrate permease variant, in which the amino acid corresponding to the 212th position is substituted with threonine, the amino acid corresponding to the 114th position is substituted with phenylalanine, or the amino acid corresponding to the 28th position is substituted with valine in the amino acid sequence of SEQ ID NO: 1, may be encoded by a polynucleotide including any one nucleic acid sequence among SEQ ID NO: 22 to SEQ ID NO: 24, but is not limited thereto.

The polynucleotide encoding the γ-aminobutyrate permease variant may include any one nucleic acid sequence among SEQ ID NO: 22 to SEQ ID NO: 24, but is not limited thereto.

As used herein, the term "polynucleotide" refers to a DNA or RNA strand having a certain length or more as a polymer of nucleotides in which nucleotide monomers are connected in a long chain form by covalent bonds. In the present application, the polynucleotide may encode a polypeptide exhibiting the activity of γ-aminobutyrate permease in which the amino acid corresponding to the 212th position is substituted with threonine, the amino acid corresponding to the 114th position is substituted with phenylalanine, or the amino acid corresponding to the 28th position is substituted with valine in the amino acid sequence of SEQ ID NO: 1, but is not limited thereto.

The polynucleotide may include, without limitation, any polynucleotide encoding a polypeptide exhibiting the activity of the γ-aminobutyrate permease according to the present application. In the present application, the gene encoding the amino acid sequence of γ-aminobutyrate permease is the aroP gene, and the gene may be derived from a microorganism belonging to *Corynebacterium* sp., and specifically, it may be derived from *Corynebacterium glutamicum*, but is not limited thereto.

Specifically, the polynucleotide encoding the polypeptide exhibiting the activity of γ-aminobutyrate permease may contain a nucleic acid sequence encoding the amino acid sequence of SEQ ID NO: 1 or an amino acid sequence in which the amino acid corresponding to the 212th position is substituted with threonine, the amino acid corresponding to the 114th position is substituted with phenylalanine, or the amino acid corresponding to the 28th position is substituted with valine in the amino acid sequence of SEQ ID NO: 1. In the polynucleotide, the coding region may be variously modified because of the degeneracy of codons or taking into account the preferred codons in the organism in which the polypeptide is to be expressed within a range in which the amino acid sequence of the polypeptide is not changed. The polynucleotide may contain, for example, the nucleic acid sequence of SEQ ID NO: 2, and may consist of a nucleic acid sequence having 80%, specifically 90% or more, more specifically 95% or more, 96% or more, 97% or more, 98% or more, or far more specifically 99% or more homology or identity thereto, but is not limited thereto.

Additionally, the polynucleotide of the present application may contain, without limitation, any sequence encoding the amino acid sequence in which the amino acid corresponding to the 212th position is substituted with threonine, the amino acid corresponding to the 114th position is substituted with phenylalanine, or the amino acid corresponding to the 28th position is substituted with valine in the amino acid sequence of SEQ ID NO: 1 by hybridizing with a probe that may be prepared from a known gene sequence, for example, a sequence complementary to all or part of the nucleic acid sequence under stringent conditions.

Specifically, in the amino acid sequence of SEQ ID NO: 1, the sequence encoding the variant in which the amino acid corresponding to the 212th position is substituted with threonine may include SEQ ID NO: 22, the variant in which the amino acid corresponding to the 114th position is substituted with phenylalanine may include SEQ ID NO: 23, and the sequence encoding the variant in which the amino acid corresponding to the 28th position is substituted with valine may include SEQ ID NO: 24, but the sequences are not limited thereto.

The "stringent condition" refers to a condition that enables specific hybridization between polynucleotides. This condition is specifically described in literatures (for example, J. Sambrook et al., supra). Examples thereof include conditions in which polynucleotides having high homology or identity to each other, for example, polynucleotides having 40% or more, specifically 90% or more, more specifically 95% or more, 96% or more, 97% or more, 98% or more, or far more specifically 99% or more homology or identity to each other hybridize with each other and polynucleotides having lower homology or identity to each other than this do not hybridize with each other; or conditions, in which washing is performed 1 time, specifically 2 to 3 times at a temperature and a salt concentration corresponding to 60° C. 1×SSC, 0.1% SDS, specifically 60° C., 0.1×SSC, 0.1% SDS, and more specifically 68° C. 0.1×SSC, 0.1% SDS, the washing conditions of usual Southern hybridization.

Hybridization requires that two nucleic acids have complementary sequences, although mismatch between the nucleic acids is possible depending on the stringency of hybridization. The term "complementary" is used to describe the relation between nucleotide bases capable of hybridizing with each other. For example, with regard to DNA, adenosine is complementary to thymine and cytosine is complementary to guanine. Accordingly, the polynucleotide of the present application may also contain substantially similar nucleic acid sequences as well as isolated nucleic acid fragments complementary to the full sequence.

Specifically, polynucleotides having homology or identity to each other may be detected using hybridization conditions including a hybridization step at a Tm value of 55° C. and the conditions described above. The Tm value may be 60° C., 63° C., or 65° C., but is not limited thereto and may be appropriately adjusted by those skilled in the art depending on the purpose.

The appropriate stringency for hybridizing polynucleotides depends on the length of the polynucleotides and the degree of complementarity, and the parameters are well known in the art (see Sambrook et al., supra, 9.50-9.51, 11.7-11.8).

Another aspect of the present application provides a vector comprising a polynucleotide encoding the γ-aminobutyrate permease variant of the present application. Specifically, there is provided a vector comprising a polynucleotide encoding a γ-aminobutyrate permease variant in which the amino acid corresponding to the 212th position is substituted with threonine, the amino acid corresponding to the 114th position is substituted with phenylalanine, or the amino acid corresponding to the 28th position is substituted with valine in the amino acid sequence of SEQ ID NO: 1.

The amino acid sequence of SEQ ID NO: 1, γ-aminobutyrate permease, variant, and polynucleotide are as described above.

As used herein, the term "vector" refers to a DNA preparation containing the nucleic acid sequence of a polynucleotide encoding a target polypeptide, operably linked to a suitable expression control region (or expression control sequence) so that the target polypeptide can be expressed in a suitable host. The expression control region may include a promoter capable of initiating transcription, an arbitrary operator sequence for regulating such transcription, a sequence encoding a suitable mRNA ribosome binding site, and a sequence controlling the termination of transcription and translation. After being transformed into a suitable host cell, the vector may be replicated or function independently of the host genome and may be integrated into the genome itself.

The vector used in the present application is not particularly limited, and an arbitrary vector known in the art may be used. Examples of commonly used vectors include plasmids, cosmids, viruses and bacteriophages in a natural or recombinant state. For example, pWE15, M13, MBL3, MBL4, IXII, ASHII, APII, t10, t11, Charon4A, and Charon21A may be used as a phage vector or cosmid vector, and a pBR system, a pUC system, a pBluescript II system, a pGEM system, a pTZ system, a pCL system, a pET system and the like may be used as a plasmid vector. Specifically, pDCM2 (Korean Patent Application Laid-Open No. 10-2020-0136813), pACYC177, pACYC184, pCL, pECCG117, pUC19, pBR322, pMW118, and pCC1BAC vectors and the like may be used.

As an example, a polynucleotide encoding a target polypeptide may be inserted into a chromosome through a vector for intracellular chromosome insertion. The insertion of a polynucleotide into a chromosome may be performed by way of an arbitrary method known in the art, for example, homologous recombination, but is not limited thereto. The vector may further include a selection marker for determining whether the chromosome is inserted. The selection marker is used to select cells transformed with the vector, that is, to determine whether a target nucleic acid molecule is inserted, and markers that impart selectable phenotypes such as drug resistance, auxotrophy, resistance to cytotoxic agents or expression of surface polypeptides may be used. In an environment treated with a selective agent, only cells expressing the selection marker survive or exhibit other expression traits, and thus transformed cells may be selected.

In the present application, the term "expression cassette" refers to a unit cassette that includes a promoter and a target gene and can thus express the target gene operably linked to the promoter. Various factors that may help the efficient expression of the target gene may be included inside or outside the gene expression cassette. The gene expression cassette may usually include a transcription termination signal, a ribosome binding site, and a translation termination signal in addition to a promoter operably linked to the target gene, but is not limited thereto.

In the present application, the term "transformation" refers to introducing a vector comprising a polynucleotide encoding a target protein into a host cell or microorganism so that the protein encoded by the polynucleotide may be expressed in the host cell. The transformed polynucleotide may include all of these regardless of whether these are inserted into the chromosome of the host cell or located outside the chromosome, as long as these can be expressed in the host cell. The polynucleotide includes DNA and RNA encoding a target protein. The polynucleotide may be introduced in any form as long as it can be introduced into and expressed in a host cell. For example, the polynucleotide may be introduced into a host cell in the form of an expression cassette, which is a gene construct including all elements necessary for self-expression. The expression cassette may usually include a promoter operably linked to the polynucleotide, a transcription termination signal, a ribosome binding site, and a translation termination signal. The expression cassette may be in the form of an expression vector capable of self-replication. The polynucleotide may be introduced into a host cell in its own form and operably linked to a sequence necessary for expression in the host cell, but is not limited thereto.

As used herein, the term "operably linked" means that a promoter sequence, which initiates and mediates transcription of the polynucleotide encoding a target polypeptide of the present application, and the gene sequence are functionally linked to each other.

The method for transforming the vector of the present application includes any method for introducing a nucleic acid into a cell, and may be performed by selecting a suitable standard technology as known in the art depending on the host cell. For example, there are electroporation, calcium phosphate ($CaPO_4$) precipitation, calcium chloride ($CaCl_2$) precipitation, microinjection, polyethylene glycol (PEG) method, DEAE-dextran method, cationic liposome method, and lithium acetate-DMSO method, but the method is not limited thereto.

Still another aspect of the present application provides a microorganism comprising any one or more of a γ-aminobutyrate permease variant in which the amino acid corresponding to the 212th position is substituted with threonine, the amino acid corresponding to the 114th position is substituted with phenylalanine, or the amino acid corresponding to the 28th position is substituted with valine in the amino acid sequence of SEQ ID NO: 1; a polynucleotide encoding the variant; and a vector comprising the polynucleotide.

In an embodiment, the microorganism of the present application may be a microorganism that produces L-isoleucine, but is not limited thereto. Specifically, the microorganism of the present application may be a microorganism that produces L-isoleucine as a target product, and may be a microorganism having increased L-isoleucine production ability by including any one or more of the variant, polynucleotide, or vector of the present application, but is not limited thereto.

The amino acid sequence of SEQ ID NO: 1, γ-aminobutyrate permease, variant, polynucleotide, vector, and L-isoleucine are as described above.

In the present application, the term "microorganism" includes both wild-type microorganisms and microorganisms in which genetic modification has occurred naturally or artificially, and is a concept including all microorganisms in which a specific mechanism is weakened or enhanced by causes such as insertion of an external gene or enhanced or weakened activity of an endogenous gene. In the present application, the microorganism may include, without limitation, any microorganism into which one or more of a γ-aminobutyrate permease variant in which the amino acid corresponding to the 212th position is substituted with threonine, the amino acid corresponding to the 114th position is substituted with phenylalanine, or the amino acid corresponding to the 28th position is substituted with valine in the amino acid sequence of SEQ ID NO: 1; a polynucleotide encoding the variant; and a vector comprising the polynucleotide is introduced or included.

In the present application, the microorganism may include one or more of the polypeptide; a polynucleotide encoding the polypeptide; and a vector comprising the polynucleotide.

The microorganism of the present application may be a microorganism having the ability to produce a target protein or a target product involved in the production of the target protein by including any one or more of the polypeptide; a polynucleotide encoding the polypeptide; and a vector comprising the polynucleotide, but is not limited thereto. The microorganism may be a microorganism having the ability to naturally produce a target protein or a target product or a microorganism in which the target protein or target product production ability is imparted to the parent strain that does not have the target protein or target product production ability, but is not limited thereto.

The microorganism is a cell or microorganism, which is transformed with a vector containing the gene encoding the polynucleotide of the present application and a target protein and expressing, for example, the target protein, and for the purposes of the present application, the host cell or microorganism may be any microorganism capable of producing a target product including the target protein.

The microorganism may be a recombinant microorganism, and the recombination may be accomplished by genetic modification such as transformation.

As used herein, the term "microorganism that produces a target protein or target product" includes both wild-type microorganisms and microorganisms in which genetic modification has occurred naturally or artificially, refers to a microorganism in which a specific mechanism is weakened or enhanced by causes such as insertion of an external gene or enhanced or inactivated activity of an endogenous gene, and may be a microorganism containing genetic modification for the production of a target protein or product.

The microorganism may be a microorganism genetically modified through any one or more of the polypeptide, a polynucleotide encoding the polypeptide, and a vector comprising the polynucleotide; a microorganism modified to express the polypeptide or a polynucleotide encoding the polypeptide; a recombinant microorganism expressing the polypeptide or a polynucleotide encoding the polypeptide; or a recombinant microorganism having the polypeptide activity, but is not limited thereto.

For the purpose of the present application, the microorganism producing a target protein or target product may be a microorganism having increased target protein or target product production ability by including the polynucleotide of the present application. Specifically, in the present application, the microorganism producing a target protein or target product or the microorganism having target protein or target product production ability may be a microorganism in which a part of a gene in the target protein or target product biosynthetic pathway is enhanced or weakened or a part of a gene in the target protein or target product degradation pathway is enhanced or weakened.

The microorganism of the present application may be a microorganism comprising one or more of a γ-aminobutyrate permease variant in which the amino acid corresponding to the 212th position is substituted with threonine, the amino acid corresponding to the 114th position is substituted with phenylalanine, or the amino acid corresponding to the 28th position is substituted with valine in the amino acid sequence of SEQ ID NO: 1; a polynucleotide encoding the variant; and a vector comprising the polynucleotide, but is not limited thereto. The microorganism of the present application may be a microorganism that produces L-isoleucine as a target product, and may have increased L-isoleucine productivity or decrease the amount of by-products generated during L-isoleucine production compared to unmodified or wild-type microorganisms, but is not limited thereto.

As used herein, the term "to be/are expressed" refers to a state in which a target protein is introduced into a microorganism or modified to be expressed in a microorganism. When the target protein is a protein present in a microorganism, the term "to be/are expressed" refers to a state in which the activity is enhanced compared to the intrinsic activity or activity before modification.

The microorganism expressing the protein variant of the present application may be a microorganism modified to express the protein variant. Accordingly, still another aspect of the present application provides a method for preparing a microorganism expressing the protein variant of the present application.

In the present application, the term "introduction of a protein" means that a microorganism exhibits the activity of a specific protein, which the microorganism did not originally have or that a microorganism exhibits improved activity compared to the intrinsic activity or activity before modification of the corresponding protein. For example, the "introduction of a protein" may refer to that a specific protein is introduced, a polynucleotide encoding a specific protein is introduced into a chromosome in a microorganism, or a vector comprising a polynucleotide encoding a specific protein is introduced into a microorganism and the activity of the specific protein is exhibited.

As used herein, the term "enhancement" of polypeptide or protein activity means that the activity of a polypeptide or protein is increased compared to the intrinsic activity. The enhancement may be used interchangeably with terms such as up-regulation, overexpression, and increase. Here, the increase may include both exhibiting activity that a polypeptide or protein did not originally have, or exhibiting improved activity compared to the intrinsic activity or activity before modification. The "intrinsic activity" refers to the activity of a specific polypeptide or protein originally possessed by the parent strain before being transformed or unmodified microorganism when the trait is changed by genetic mutation due to natural or artificial factors. This may be used interchangeably with "activity before modification". The fact that the activity of a polypeptide or protein is "enhanced" or "increased" compared to the intrinsic activity means that the activity of a polypeptide or protein is improved compared to the activity of a specific polypeptide or protein originally possessed by the parent strain before being transformed or unmodified microorganism. As an example, the activity of a polypeptide or protein may be improved by at least 1%, 3%, 5%, 10%, 25%, 50%, 75%, 100%, 125%, 150%, 200%, 250%, 300%, 350%, 400%, or 500% and at most 1000% or 2000% compared to the protein activity of the parent strain before being transformed or unmodified microorganism, but the enhancement of or increase in the activity of a polypeptide or protein is not limited thereto. The term "about" is a range including all of ±0.5, ±0.4, ±0.3, ±0.2, ±0.1, and the like, and includes all numerical values in a range equivalent or similar to the numerical value following the term about, but is not limited thereto.

The "increase in activity" may be achieved by introducing an exogenous polypeptide or protein or enhancing the activity of an endogenous polypeptide or protein, but may specifically be achieved by enhancing the activity of an endogenous polypeptide or protein. Whether or not the activity of a polypeptide or protein is enhanced may be confirmed from the increase in the activity degree or expression level of the corresponding polypeptide or protein or the amount of a product excreted from the corresponding protein.

The enhancement of the activity of a polypeptide or protein may not be limited as long as various methods well known in the art can be applied and the activity of a target polypeptide or protein can be enhanced compared to the microorganism before being modified. The method is not limited thereto, but may use genetic engineering and/or protein engineering well known to those skilled in the art, which are routine methods of molecular biology (Sitnicka et al. Functional Analysis of Genes. Advances in Cell Biology. 2010, Vol. 2. 1-16, Sambrook et al. Molecular Cloning 2012, etc.).

The method for enhancing the activity of a polypeptide or protein using the genetic engineering may be performed by way of, for example, 1) an increase in the intracellular copy number of a gene or polynucleotide encoding the polypeptide or protein,
2) a method in which the gene expression control region on a chromosome encoding the polypeptide or protein is replaced with a sequence exhibiting strong activity,
3) a method in which the nucleic acid sequence of the start codon or 5'-UTR region of the polypeptide or protein is modified,
4) a method in which a polynucleotide sequence on a chromosome is modified to increase the polypeptide or protein activity.
5) introduction of an exogenous polynucleotide exhibiting the polypeptide or protein activity or a codon-optimized modified polynucleotide of the polynucleotide, or
6) a combination of the methods, but is not limited thereto.

The method for enhancing the activity of a polypeptide or protein using the protein engineering may be performed by way of, for example, a method in which the tertiary structure of the polypeptide or protein is analyzed to select an exposed site and the exposed site is modified or chemically modified, but is not limited thereto.

1) The increase in the intracellular copy number of a gene or polynucleotide encoding the polypeptide or protein may be achieved by an arbitrary method known in the art, for example, by introducing into a host cell a vector capable of replicating and functioning independently of a host, to which a gene or polynucleotide encoding the corresponding polypeptide or protein is operably linked. Alternatively, 1) the increase may be achieved by introducing into a host cell a vector capable of inserting the gene or polynucleotide into a chromosome in the host cell, to which the gene is operably linked, but is not limited thereto. The vector is as described above.

2) The method, in which the gene expression control region (or expression control sequence) on a chromosome encoding the polypeptide or protein is replaced with a sequence exhibiting strong activity, may be performed by way of an arbitrary method known in the art, for example, by inducing a mutation in the sequence by deletion, insertion, non-conservative or conservative substitution of a nucleic acid sequence or a combination thereof to further enhance the activity of the expression control region, or by replacing the expression control region with a nucleic acid sequence exhibiting far stronger activity. The expression control region may include, but is not particularly limited to, a promoter, an operator sequence, a sequence encoding a ribosome binding site, a sequence controlling the termination of transcription and translation, and the like. The method may specifically be to link a strong heterologous promoter instead of the native promoter, but is not limited thereto.

Examples of known strong promoters include, but are not limited to, the cj1 to cj7 promoters (U.S. Pat. No. 7,662,943 B2), the lac promoter, the trp promoter, the trc promoter, the tac promoter, the lambda phage PR promoter, the PL promoter, the tet promoter, the gapA promoter, the SPL7 promoter, the SPL13(sm3) promoter (U.S. patent Ser. No. 10/584,338 B2), the 02 promoter (U.S. patent Ser. No. 10/273,491 B2), the tkt promoter, and the yccA promoter.

3) The method, in which the nucleic acid sequence of the start codon or 5'-UTR region of the polypeptide or protein is modified, may be an arbitrary method known in the art, for example, may be to substitute the endogenous start codon of the polypeptide or protein with another start codon having a higher expression level of the polypeptide or protein than the endogenous start codon, but is not limited thereto.

4) The method, in which a polynucleotide sequence on a chromosome is modified to increase the polypeptide or protein activity, may be performed by way of an arbitrary method known in the art, for example, by inducing a mutation in the expression control sequence by deletion, insertion, non-conservative or conservative substitution of a nucleic acid sequence, or a combination thereof to further enhance the activity of the polynucleotide sequence, or by replacing the polynucleotide sequence with a polynucleotide sequence improved to exhibit far stronger activity. The replacement may specifically be to insert the gene into the chromosome by homologous recombination, but is not limited thereto.

The vector used in this case may further include a selection marker for confirming whether or not the chromosome is inserted. The selection marker is as described above.

5) The introduction of an exogenous polynucleotide exhibiting the polypeptide or protein activity may be achieved by an arbitrary method known in the art, for example, by introducing into a host cell an exogenous polynucleotide encoding a polypeptide or protein exhibiting activity the same as/similar to that of the polypeptide or protein or a codon-optimized modified polynucleotide thereof. As the exogenous polynucleotide, any exogenous polynucleotide may be used without limitation in origin or sequence as long as it exhibits activity the same as/similar to that of the polypeptide or protein. The optimized codon of the exogenous polynucleotide may be introduced into the host cell so that the optimized transcription and translation of the introduced exogenous polynucleotide are performed in the host cell. The introduction may be performed by appropriately selecting a known transformation method by those skilled in the art, and a polypeptide or protein is produced, and its activity may be increased as the introduced polynucleotide is expressed in the host cell.

Finally, 6) the combination of the methods may be performed by applying any one or more of the methods 1) to 5) together.

Such enhancement of polypeptide or protein activity may be an increase in the activity or concentration of the corresponding polypeptide or protein based on the activity or concentration of the polypeptide or protein expressed in a wild-type microbial strain or a microbial strain before being modified or an increase in the amount of a product produced from the corresponding polypeptide or protein, but is not limited thereto.

As used herein, the term "strain before being modified" or "microorganism before being modified" does not exclude strains containing mutations that may occur naturally in microorganisms, and may refer to a wild-type strain or a natural strain itself, or a strain before the trait is changed by genetic mutation due to natural or artificial factors. The "strain before being modified" or "microorganism before being modified" may be used interchangeably with "unmutated strain", "unmodified strain", "unmutated microorganism", "unmodified microorganism", or "reference microorganism".

In an embodiment, the microorganism of the present application may belong to *Corynebacterium* sp., but is not limited thereto.

The "microorganism belonging to *Corynebacterium* sp." of the present application may include all microorganisms belonging to *Corynebacterium* sp. The microorganism belonging to *Corynebacterum* sp. may be specifically *Corynebacterium glutamicum, Corynebacterium crudilactis, Corynebacterium deserti, Corynebacterium efticiens, Corynebacterium callunae, Corynebacterium stationis, Corynebacterium singulare, Corynebacterum halotolerans, Corynebacterium stratum, Corynebacterium ammoniagenes, Corynebacterium pollutisoli, Corynebacterium imitans, Corynebacterium testudinoris* or *Corynebacterium flavescens*, more specifically *Corynebacterum glutamicum, Corynebacterium callunae, Corynebacterium crenatum*, or *Corynebacterium deserti.*

In the present application, the parent strain of the microorganism may be a microorganism in which the biosynthetic pathway of L-isoleucine is additionally enhanced to increase the production of L-isoleucine, but is not limited thereto.

Specifically, in order to enhance the biosynthetic pathway of L-isoleucine, the microorganism may be, for example, a microorganism in which the aroP promoter is substituted with the gapA promoter to enhance the function of the promoter, a genetic mutation (R407H) is additionally introduced into the hom gene encoding homoserine dehydrogenase to resolve feedback inhibition of threonine, a precursor of isoleucine (Korean Registered Patent No. 10-1996769), genetic mutations (T381A,F383A) of the ilvA gene encoding L-threonine dehydratase are introduced (Korean Patent Application No. 10-2020-0078669), or a genetic mutation (L377K) is additionally introduced into the lysC gene encoding aspartokinase (U.S. Registration Publication No. 10662450 B2). However, the microorganism is not limited to the above, and the production of L-isoleucine may be increased by way of a gene expression control method known in the art.

As another example for increasing the production of L-isoleucine, in the present application, the parent strain of the microorganism may be a microorganism in which a gene that weakens the biosynthetic pathway of L-isoleucine is additionally inactivated to increase the production of L-isoleucine, but is not limited thereto.

As used herein, the term "inactivation" or "weakening" of a polypeptide or protein is a concept including both decreased activity compared to the intrinsic activity or no activity. The inactivation or weakening may be used interchangeably with terms such as down-regulation, decrease, and reduce. The inactivation or weakening may also include a case where the activity of a protein itself is decreased or eliminated compared to the activity of a protein possessed by the native microorganism because of mutation of the gene encoding the protein, and the like, a case where the overall protein activity degree in the cell is lower than that of the natural strain because of expression inhibition or translation inhibition of the gene encoding this, a case where the expression of the gene does not occur at all, and a case where the gene does not exhibit activity although the gene is expressed. The "intrinsic activity" refers to the activity of a specific polypeptide or protein originally possessed by the parent strain before being transformed or unmodified microorganism when a trait is changed by genetic mutation due to natural or artificial factors. This may be used interchangeably with "activity before modification". The fact that the activity of a polypeptide or protein is "decreased" compared to the intrinsic activity means that the activity is lowered compared to the activity of a specific polypeptide or protein originally possessed by the parent strain before being transformed or unmodified microorganism.

Such inactivation of a protein or weakening of the activity may be achieved by application of various methods well known in the art, but is not limited thereto (Nakashima N. et al., Bacterial cellular engineering by genome editing and gene silencing. *Int J Mol Sci.* 2014; 15(2):2773-2793, Sambrook et al. *Molecular Cloning* 2012, etc.).

Examples of the methods include, 1) a method in which all or part of the gene encoding the protein is deleted;
2) modification of the expression control region (or expression control sequence) to decrease the expression of the gene encoding the protein;
3) modification of the gene sequence encoding the protein so that the activity of the protein is eliminated or weakened;
4) introduction of an antisense oligonucleotide (for example, antisense RNA) that complementarily binds to the transcript of the gene encoding the protein;
5) a method in which a secondary structure is formed by adding a sequence complementary to the Shine-Dalgamo sequence to the front end of the Shine-Dalgamo sequence of the gene encoding the protein to make attachment of ribosome impossible; and 6) a method in which a promoter transcribed in the opposite direction to the 3' end of the open reading frame (ORF) of the polynucleotide sequence of the gene encoding the protein is added (reverse transcription engineering, RTE), and the inactivation of a protein or weakening of the activity may also be achieved by a combination thereof, but is not particularly limited thereto.

Specifically, the method, in which all or part of the gene encoding the protein is deleted, may be performed by replacing a polynucleotide encoding an endogenous target protein in a chromosome with a polynucleotide or a marker gene in which some nucleotide sequences are deleted through a vector for chromosome insertion in a microorganism. As an example of such a method in which part or all of a polynucleotide is deleted, a method in which a polynucleotide is deleted via homologous recombination may be used, the method is not limited thereto.

The method, in which all or part of the gene is deleted, may be performed by inducing mutations using light such as ultraviolet rays or chemical substances and selecting strains lacking the target gene from the obtained mutants. The gene deletion method includes a method by DNA recombination technology. In the DNA recombination technology, the gene deletion may be achieved by, for example, injecting a nucleic acid sequence or vector containing a nucleic acid sequence homologous to a target gene into the microorganism to cause homologous recombination. The injected nucleic acid sequence or vector may include a dominant selection marker, but is not limited thereto.

The method, in which the expression control sequence is modified, may be performed by applying various methods well known in the art. As an example, the method may be performed by inducing mutations in the expression control region (or expression control sequence) by deletion, insertion, non-conservative or conservative substitution of the polynucleotide sequence or a combination thereof so that the activity of the expression control region (or expression control sequence) is further weakened, or by replacing the polynucleotide sequence with a polynucleotide sequence exhibiting far weaker activity. The expression control region includes a promoter, an operator sequence, a sequence encoding a ribosome binding site, and a sequence regulating the termination of transcription and translation, but is not limited thereto.

The method, in which the gene sequence is modified, may be performed by inducing mutations in the sequence by deletion, insertion, non-conservative or conservative substitution of a gene sequence, or a combination thereof so that the activity of the polypeptide is further weakened, or by replacing the gene sequence with a gene sequence improved to exhibit far weaker activity or a gene sequence improved not to exhibit activity, but is not limited thereto.

For example, the expression of a gene may be inhibited or weakened by introducing mutation into the gene sequence to form a stop codon.

Another aspect of the present application provides a method for producing L-isoleucine. Specifically, the method provides a method, comprising culturing a microorganism comprising one or more of a γ-aminobutyrate permease variant, in which the amino acid corresponding to the 212th position is substituted with threonine, the amino acid corresponding to the 114th position is substituted with phenylalanine, or the amino acid corresponding to the 28th position is substituted with valine in the amino acid sequence of SEQ ID NO: 1; a polynucleotide encoding the variant; and a vector comprising the polynucleotide in a medium.

Another aspect of the present application provides a method for decreasing the amount of by-products generated during the production of L-isoleucine. Specifically, the method provides a method, comprising culturing a microorganism comprising one or more of a γ-aminobutyrate permease variant, in which the amino acid corresponding to the 212th position is substituted with threonine, the amino acid corresponding to the 114th position is substituted with phenylalanine, or the amino acid corresponding to the 28th position is substituted with valine in the amino acid sequence of SEQ ID NO: 1; a polynucleotide encoding the variant; and a vector comprising the polynucleotide in a medium.

The L-isoleucine, amino acid of SEQ ID NO: 1, γ-aminobutyrate permease, variant, polynucleotide, vector, and microorganism are as described above.

The microorganism may belong to *Corynebacterium* sp., specifically *Corynebacterium glutamicum*, but is not limited thereto. This is as described above.

In the present application, the term "culture" means growing the microorganism in an appropriately controlled environmental condition. The culture process of the present application may be performed according to a suitable medium and culture conditions known in the art. Such a culture process may be easily adjusted and used by those skilled in the art depending on the selected strain. Specifically, the culture may be batch culture, continuous culture, and fed-batch culture, but is not limited thereto.

As used herein, the term "medium" refers to a material in which nutrients necessary for culturing the microorganism are mixed as main components, and supplies nutrients and growth factors, including water, which are essential for survival and development. Specifically, as the medium and other culture conditions used for culturing the microorganism of the present application, any medium may be used without any particular limitation as long as it is a medium conventionally used for culturing microorganisms. The microorganism of the present application may be cultured in a conventional medium containing appropriate carbon sources, nitrogen sources, phosphorus sources, inorganic compounds, amino acids and/or vitamins, and the like under an aerobic condition while controlling the temperature, pH and the like.

In the present application, the carbon sources may include carbohydrates such as glucose, saccharose, lactose, fructose, sucrose, and maltose; sugar alcohols such as mannitol and sorbitol; organic acids such as pyruvic acid, lactic acid, and citric acid: and amino acids such as glutamic acid, methionine, and lysine. Natural organic nutrients such as starch hydrolysates, molasses, blackstrap molasses, rice bran, cassava, sugarcane waste and corn steep liquor may be used. Specifically, carbohydrates such as glucose and sterilized pre-treated molasses (namely, molasses converted to reducing sugar) may be used. Appropriate amounts of other carbon sources may be variously used without limitation. These carbon sources may be used singly or in a combination of two or more kinds thereof, but the carbon sources are not limited thereto.

As the nitrogen sources, inorganic nitrogen sources such as ammonia, ammonium sulfate, ammonium chloride, ammonium acetate, ammonium phosphate, ammonium carbonate, and ammonium nitrate; and organic nitrogen sources such as amino acids such as glutamic acid, methionine, and glutamine, peptone. NZ-amine, meat extract, yeast extract, malt extract, corn steep liquor, casein hydrolysates, fish or decomposition products thereof, and defatted soybean cake or decomposition products thereof may be used. These nitrogen sources may be used singly or in a combination of two or more kinds thereof, but the nitrogen sources are not limited thereto.

The phosphorus sources may include potassium phosphate monobasic, potassium phosphate dibasic, or a sodium-containing salt corresponding thereto. As the inorganic compounds, sodium chloride, calcium chloride, iron chloride, magnesium sulfate, iron sulfate, manganese sulfate, calcium carbonate and the like may be used, and the inorganic compounds may include amino acids, vitamins and/or suitable precursors in addition to these. These components or precursors may be added to the medium either batchwise or continuously. However, the medium is not limited thereto.

During the culture of the microorganism, compounds such as ammonium hydroxide, potassium hydroxide, ammonia, phosphoric acid, and sulfuric acid may be added to the medium in an appropriate manner to adjust the pH of the medium. During the culture, an antifoaming agent such as fatty acid polyglycol ester may be used to suppress bubble formation. Oxygen or oxygen-containing gas may be injected into the medium in order to maintain the aerobic state of the medium, or nitrogen, hydrogen or carbon dioxide gas may be injected or gas may not be injected in order to maintain the anaerobic and microaerobic states, but the conditions are not limited thereto.

The temperature of the medium may be 20° C. to 50° C., specifically 30° C. to 37° C., but is not limited thereto. The culture may be continuously performed until a desired production amount of useful substance is obtained, and the culture period may specifically be 10 hours to 100 hours, but is not limited thereto.

Specifically, the culture medium for a *Corynebacterium* sp. strain may be found in the literature ("Manual of Methods for General Bacteriology" by the American Society for Bacteriology (Washington D.C., USA, 1981)), but is not limited thereto.

In an embodiment, the method for producing L-isoleucine, the method for preparing L-isoleucine, or the method for decreasing the amount of by-products generated during the production of L-isoleucine may further include recovering L-isoleucine from the medium or microorganism, but is not limited thereto.

The method for recovering L-isoleucine may be collecting the desired L-isoleucine using a suitable method known in the art according to the method for culturing a microorganism of the present application, for example, a batch, continuous or fed-batch culture method. For example, centrifugation, filtration, treatment with a crystallized protein precipitating agent (salting out method), extraction, ultrasonic disruption, ultrafiltration, dialysis, various types of chromatography such as molecular sieve chromatography (gel filtration), adsorption chromatography, ion exchange chromatography, affinity chromatography, and HPLC, and a combination of these methods may be used, and the desired L-isoleucine may be recovered from the medium or microorganism using any suitable method known in the art.

The production method may include an additional purification process. In the purification process, the recovered L-isoleucine may be purified using any suitable method known in the art. The recovered L-isoleucine may be in a purified form or a microbial fermentation broth containing the desired product (*Introduction to Biotechnology and Genetic Engineering*. A. J. Nair, 2008).

In an embodiment, the method for producing L-isoleucine or the method for preparing L-isoleucine may be to decrease the amount of by-products generated during the production of L-isoleucine, but is not limited thereto.

In the present application, the term "by-product" includes all substances that may be generated during the production of L-isoleucine. The by-product may be any one or more selected from α-aminobutyrate (AABA) or arginine (Arg, R), histidine (His, H), glutamic acid (Glu, E), aspartic acid (Asp, D), glycine (Gly, G), alanine (Ala, A), valine (Val, V), leucine (Leu, L), methionine (Met, M), phenylalanine (Phe, F), tryptophan (Trp, W), proline (Pro, P), serine (Ser, S), cysteine (Cys, C), tyrosine (Tyr, Y), asparagine (Asn, N) and glutamine (Gin, Q) that are amino acids other than L-isoleucine, but are not limited thereto. For the purpose of the present application, the by-product may be any one or more selected from the group consisting of α-aminobutyrate (AABA), valine, phenylalanine, and leucine, may specifically be α-aminobutyrate or valine, but is not limited thereto.

Another aspect of the present application provides a composition for L-isoleucine production. Specifically, the composition provides a microorganism comprising one or more of a γ-aminobutyrate permease variant, in which the amino acid corresponding to the 212th position is substituted with threonine, the amino acid corresponding to the 114th position is substituted with phenylalanine, or the amino acid corresponding to the 28th position is substituted with valine in the amino acid sequence of SEQ ID NO: 1; a polynucleotide encoding the variant; and a vector comprising the polynucleotide, or a culture of the microorganism.

The amino acid of SEQ ID NO: 1, γ-aminobutyrate permease, variant, polynucleotide, vector, microorganism, and culture are as described above.

The composition for L-isoleucine production may refer to a composition from which L-isoleucine can be highly efficiently produced by the γ-aminobutyrate permease variant of the present application. The composition may include, without limitation, the γ-aminobutyrate permease variant or a configuration capable of operating the γ-aminobutyrate permease variant. The γ-aminobutyrate permease variant may be in the form of being included in a vector so that the operably linked gene can be expressed in the introduced host cell.

The composition may further include a cryoprotectant or an excipient. The cryoprotectant or excipient may be a substance that does not occur naturally or a naturally occurring substance, but is not limited thereto. In another embodiment, the cryoprotectant or excipient may be a substance that the strain does not naturally contact, or a substance that is not naturally included at the same time along with the strain, but is not limited thereto.

Another aspect of the present application is to provide use a γ-aminobutyrate permease variant, wherein an amino acid corresponding to position 212 is substituted with threonine, an amino acid corresponding to position 114 is substituted with phenylalanine, or an amino acid corresponding to position 28 is substituted with valine in an amino acid sequence of SEQ ID NO: 1; or a microorganism comprising the variant, a polynucleotide encoding the variant; and a vector comprising the polynucleotide, for production of L-isoleucine.

The variant, polynucleotide, vector, microorganism, and isoleucine are as described above.

Forms for Implementation of the Invention

Hereinafter, the present application will be described in more detail with reference to Examples. However, these Examples and Experimental Examples are for illustrative purposes of the present application, and the scope of the present application is not limited to these Examples and Experimental Examples.

Reference Example 1: Construction of Vector for aroP Gene Overexpression

According to the purpose of the present application, in order to more clearly confirm the transformation due to the aroP gene encoding γ-aminobutyrate permease and a variant thereof, the aroP gene was overexpressed in the *Corynebacterium glutamicum* ATCC13032 strain.

In order to overexpress the aroP gene encoding γ-aminobutyrate permease, a plasmid vector was constructed in which the aroP promoter was enhanced by replacing the aroP gene promoter with the gapA promoter.

In order to construct a strain in which the aroP promoter was substituted with the gapA promoter, PCR was performed using the ATCC13032 chromosome as a template and primers of SEQ ID NO: 4 and SEQ ID NO: 5, SEQ ID NO: 6 and SEQ ID NO: 7, or SEQ ID NO: 8 and SEQ ID NO: 9. The primers used to perform each of the PCRs are as presented in Table 1 below.

TABLE 1

| SEQ ID NO: | Name | Sequence |
|---|---|---|
| 4 | primer | AATTCGAGCTCGGTACCCTTCCCCCTGGAGTCCGCA |
| 5 | primer | ATAGGCTCGGTCGTTTTTAGGCTTGTATCAACCGTAAACCCA |
| 6 | primer | TGGGTTTACGGTTGATACAAGCCTAAAAACGACCGAGCCTAT |
| 7 | primer | CCTTCATTAGATTTAGCCATGTGTCTCCTCTAAAGATTGT |
| 8 | primer | ACAATCTTTAGAGGAGACACATGGCTAAATCTAATGAAGG |
| 9 | primer | GTCGACTCTAGAGGATCCCCTCAGTTCAAGTCGGAAGGGGTGCGA |

PfuUltra™ high-fidelity DNA polymerase (Stratagene) was used as a polymerase for the PCR reaction, in which the PCR conditions were denaturation at 95° C. for 30 seconds; annealing at 55° C. for 30 seconds; and polymerization at 72° C. for 1 minute, and the denaturation, annealing, and polymerization under these conditions were repeated 28 times. As a result, a 1,000 bp DNA fragment at the 5' upstream region and a 1,392 bp DNA fragment at the 3' downstream region with reference to the gapA promoter portion and the aroP gene start codon were obtained, respectively. PCR was performed again using the three amplified DNA fragments as a template and primers of SEQ ID NO: 4 and SEQ ID NO: 9. As the PCR conditions, denaturation at 95° C. for 5 minutes, then denaturation at 95° C. for 30 seconds; annealing, and polymerization at 72° C. for 2 minutes were repeated 6 times, then denaturation at 95° C. for 30 seconds; annealing at 55° C. for 30 seconds; and polymerization at 72° C. for 2 minutes were repeated 20 times, and then polymerization was performed at 72° C. for 5 minutes. As a result, a 2.4 kb DNA fragment encoding the aroP gene including gapA promoter was amplified. The amplification product was purified using QUIAGEN's PCR purification kit and used as an insert DNA fragment for vector construction.

Meanwhile, the insert DNA fragment, which was amplified by the PCR above, were mixed with pDCM2 vector, which was digested with a restriction enzyme SmaI and then heat-treated at 65° C. for 20 minutes, at a 1:2 molar ratio (M), and the insert DNA fragment was cloned into the pDCM2 vector using TaKaRa's infusion cloning kit according to the manufacturer's manual provided, and thereby a vector pDCM2-PgapA-aroP, in which aroP promoter is substituted with gapA promoter to be introduced into a chromosome, was constructed.

Reference Example 2: Preparation of Strain Producing L-Isoleucine

Wild-type *Corynebacterium glutamicum* has the ability to produce L-isoleucine, but does not overproduce L-isoleucine. Hence, in order to confirm the genetic trait that increases the L-isoleucine production ability according to the purpose of the present application, a strain having increased L-isoleucine production ability was used.

First, a strain producing L-isoleucine was developed from wild-type *Corynebacterum glutamicum* ATCC13032. Specifically, in order to resolve feedback inhibition of threonine, a precursor of isoleucine, in the L-isoleucine biosynthetic pathway, arginine, which was the 407th amino acid of homoserine dehydrogenase, was substituted with histidine by mutating the hom gene encoding homoserine dehydrogenase (Korean Registered Patent No. 10-1996769). Specifically, the polynucleotide sequence encoding hom (R407H) was shown in SEQ ID NO: 10.

Specifically, in order to prepare strains into which a hom(R407H) mutation was introduced, PCR was performed using the chromosome of *Corynebacterium glutamicum* ATCC13032 as a template and primers of SEQ ID NO: 11 and SEQ ID NO: 12 or SEQ ID NO: 13 and SEQ ID NO: 14, respectively. The primer sequences used to perform each of the PCRs are as presented in Table 2 below.

TABLE 2

| SEQ ID NO: | Name | Sequence |
|---|---|---|
| 11 | primer | TCGAGCTCGGTACCCCGCTTTTGCACTCATCGAGC |
| 12 | primer | CACGATCAGATGTGCATCATCAT |
| 13 | primer | ATGATGATGCACATCTGATCGTG |
| 14 | primer | CTCTAGAGGATCCCCGAGCATCTTCCAAAACCTTG |

PfuUltra™ high-fidelity DNA polymerase (Stratagene) was used as a polymerase for the PCR reaction, the PCR conditions were denaturation at 95° C. for 30 seconds; annealing at 55° C. for 30 seconds; and polymerization at 72° C. for 1 minute, and the denaturation, annealing, and polymerization under these conditions were repeated 28 times. As a result, a 1,000 bp DNA fragment at the 5' upstream region and a 1,000 bp DNA fragment at the 3' downstream region with reference to the hom gene mutation were obtained, respectively.

PCR was performed using the two amplified DNA fragments as a template and primers of SEQ ID NO: 11 and SEQ ID NO: 14. As the PCR conditions, denaturation at 95° C. for 5 minutes, then denaturation at 95° C. for 30 seconds; annealing at 55° C. for 30 seconds; and polymerization at 72° C. for 2 minutes were repeated 28 times, and then polymerization was performed at 72° C. for 5 minutes.

As a result, a 2 kb DNA fragment containing a mutation of the hom gene encoding a homoserine dehydrogenase variant, in which the 407th arginine was substituted with histidine, was amplified. The amplification product was purified using a PCR purification kit (QUIAGEN) and used as an insert DNA fragment for vector construction. The pDCM2 vector (Korean Patent Application Publication No. 10-2020-0136813), which was heat-treated at 65° C. for 20 minutes, and the purified amplification product were both digested with a restriction enzyme SmaI and at a 1:2 molar ratio (M), and the purified amplification product was cloned into the pDCM2 vector using TaKaRa's infusion cloning kit according to the manufacturer's manual provided, and thereby a vector pDCM2-R407H for introducing hom (R407H) mutation into a chromosome was constructed.

The constructed vector was transformed into *Corynebacterium glutamicum* ATCC13032 via electroporation, and followed by a secondary crossover process to obtain a strain containing hom(R407H) mutation on the chromosome, which was named *Corynebacterium glutamicum* ATCC13032 hom(R407H).

In order to release the feedback and increase the activity with respect to L-isoleucine of the prepared ATCC13032 hom(R407H) strain, threonine, which was the 381st amino acid of L-threonine dehydratase (SEQ ID NO: 25), was substituted with alanine; and phenylalanine, which was the 383rd amino acid of L-threonine dehydratase, was substituted with alanine by mutating ilvA, a gene encoding L-threonine dehydratase. Specifically, a strain into which ilvA(T381A, F383A) was introduced was prepared, and the polynucleotide encoding ilvA(T381A, F383A) is represented by SEQ ID NO: 15.

Specifically, in order to prepare strains into which the ilvA(T381A, F383A) mutation was introduced, PCR was performed using the chromosome of *Corynebacterium glutamicum* ATCC13032 as a template and primers of SEQ ID NO: 16 and SEQ ID NO: 17 or SEQ ID NO: 18 and SEQ ID NO: 19. The primer sequences used to perform each of the PCRs are as presented in Table 3 below.

TABLE 3

| SEQ ID NO: | Name | Sequence |
|---|---|---|
| 16 | primer | TCGAGCTCGGTACCCATGAGTGAAACATACGTGTC |
| 17 | primer | GCGCTTGAGGTACTCtgcCAGCGcGATGTCATCATCCGG |
| 18 | primer | CCGGATGATGACATCgCGCTGgcaGAGTACCTCAAGCGC |
| 19 | primer | CTCTAGAGGATCCCCCGTCACCGACACCTCCACA |

PfuUltra™ high-fidelity DNA polymerase (Stratagene) was used as a polymerase for the PCR reaction, the PCR conditions were denaturation at 95° C. for 30 seconds; annealing at 55° C. for 30 seconds; and polymerization at 72° C. for 1 minute, and the denaturation, annealing, and polymerization under these conditions were repeated 28 times. As a result, a 1,126 bp DNA fragment at the 5' upstream region and a 286 bp DNA fragment at the 3' downstream region with reference to the mutation of the ilvA gene were obtained, respectively.

PCR was performed using the two amplified DNA fragments as a template and primers of SEQ ID NO: 16 and SEQ ID NO: 19. As the PCR conditions, denaturation at 95° C. for 5 minutes, then denaturation at 95° C. for 30 seconds: annealing at 55° C. for 30 seconds: and polymerization at 72° C. for 2 minutes were repeated 28 times, and then polymerization was performed at 72° C. for 5 minutes.

As a result, a 1.4 kb DNA fragment containing a mutation of the ilvA gene encoding the L-threonine dehydratase variant, in which the 381st threonine was substituted with alanine and the 383rd phenylalanine was substituted with alanine, was amplified. The amplification product was purified using a PCR purification kit (QUIAGEN) and used as an insert DNA fragment for vector construction. The pDCM2 vector (Korean Patent Application Publication No. 10-2020-0136813), which was heat-treated at 65° C. for 20 minutes, and the purified amplification product were both digested with a restriction enzyme SmaI and at a 1:2 molar ratio (M), and the purified amplification product was cloned into the pDCM2 vector using TaKaRa's infusion cloning kit according to the manufacturer's manual provided, and thereby a vector pDCM2-ilvA(T381A, F383A) for introducing ilvA (T381A, F383A) mutation into a chromosome was constructed.

The constructed vector was transformed into *Corynebacterium glutamicum* ATCC13032 hom(R407H) via electroporation, and followed by a secondary crossover process to obtain a strain containing ilvA(T381A, F383A) mutation on the chromosome, which was named *Corynebacterium glutamicum* CA10-3101.

The strain CA10-3101 was internationally deposited with the Korean Culture Center of Microorganisms (KCCM), an international depository under the Budapest Treaty, as of May 27, 2020, and was given a deposit number as KCCM12739P.

For reference, in order to confirm whether the introduction of ilvA(T381A, F383A) into the L-isoleucine-producing strain releases the feedback and increases the activity with respect to L-isoleucine and thus increases the L-isoleucine productivity efficiency, the following experiment was performed. Specifically, the concentrations of L-isoleucine and L-threonine in the KCCM11248P/pECCG117-ilvA (T381A, F383A) strain culture in which the ilvA(T381A, F383A) mutation was introduced into the KCJI-38 (KCCM11248P. Korean Registered Patent No. 10-1335789) strain, which was a NTG (N-methyl-N'-nitro-N-nitrosoguanidine)-treated L-isoleucine-producing strain, by way of an electric pulse method were measured and the results are presented in Table 4 below.

TABLE 4

| Strain name | L-Isoleucine (g/L) | L-Threonine (g/L) |
|---|---|---|
| KCCM11248P | 1.5 | 0.5 |
| KCCM11248P/ pECCG117-ilvA(F383A) | 2.8 | 0.6 |
| KCCM11248P/ pECCG117-ilvA(T381A, F383A) | 4.0 | 0.0 |

As presented in Table 4, it was confirmed that the production of L-isoleucine is significantly increased and the degradation rate of L-threonine is higher in the KCCM11248P/pECCG117-ilvA(T381A, F383A) strain into which ilvA(T381A,F383A) mutation is introduced compared to the KCCM11248P or KCCM11248P/pECCG117-ilvA(F383A) strain. In other words, it was confirmed that introduction of the ilvA(T381A, F383A) mutation released the feedback and increased the activity with respect to L-isoleucine for the purpose of the present application.

Example 1: Preparation of L-Isoleucine-Producing Strain Overexpressing aroP Gene and Confirmation of Effect of aroP on Fermentation Purity of L-Isoleucine In order to confirm whether aroP overexpression or mutation during L-isoleucine production decreases the amount of by-products and increases the purity of L-isoleucine, the aroP gene was enhanced. To this end, CA10-3101, which was the L-isoleucine-producing strain prepared in Reference Example 2, was targeted. Specifically, the vector constructed in Reference Example 1 was transformed into *Corynebacterium glutamicum* CA10-3101 via electroporation, and followed by a secondary crossover process to obtain a strain in which the aroP promoter was enhanced on the chromosome, and this strain was named *Corynebacterum glutamicum* CA10-3117. The parent strain (CA10-3101) and the aroP-enhanced strain (CA10-3117) were inoculated into 250 mL corner-baffle flasks containing 25 mL of isoleucine production medium, respectively, and then cultured at 32° C. for 60 hours with shaking at 200 rpm to prepare L-isoleucine. The composition of the production medium used in the present Example is as follows.

<Production Medium>

Glucose: 10%, yeast extract: 0.2%, ammonium sulfate: 1.6%, potassium phosphate monobasic: 0.1%, magnesium sulfate heptahydrate: 0.1%, iron sulfate heptahydrate: 10 mg/L, manganese sulfate monohydrate: 10 mg/L, biotin: 200 μg/L, and pH: 7.2

After completion of the culture, the productions of L-isoleucine and by-products were measured using high-performance liquid chromatography (HPLC), and the concentrations of L-isoleucine and by-products in the culture of each strain subjected to the experiment are presented in Table 5 below.

TABLE 5

| Strain name | L-Isoleucine concentration (g/L) | AABA concentration (g/L) | L-Valine concentration (g/L) |
|---|---|---|---|
| CA10-3101 (parent strain) | 2.5 | 0.9 | 1.4 |
| CA10-3117 (aroP-enhanced strain) | 2.7 | 0.4 | 1.1 |

As a result, as presented in Table 5, *Corynebacterium glutamicum* CA10-3101, the parent strain, produced L-isoleucine at a concentration of 2.5 g/L and α-ketobutyrate (AABA) and L-valine, the major by-products, were detected at 0.9 g/L and 1.4 g/L, respectively, but *Corynebacterium glutamicum* CA10-3117, a *Corynebacterium glutamicum* aroP-enhanced strain, prepared in the present Example produced L-isoleucine at a concentration of 2.7 g/L and was thus confirmed to exhibit L-isoleucine productivity increased by 108% compared to that of the parent strain. In addition, by-products α-ketobutyrate and valine were detected at 0.4 g/L and 1.1 g/L, respectively, and it was thus confirmed that the amounts of by-products α-ketobutyrate and valine produced by the strain prepared in the present Example were decreased by 55% and 21%, respectively, compared to those of by-products α-ketobutyrate and valine produced by the parent strain.

Based on the results above, it was confirmed that the aroP gene can be a target for increasing the fermentation purity of L-isoleucine by decreasing the amount of by-products of L-isoleucine and increasing the productivity of L-isoleucine. Accordingly, a random mutagenesis method was used to further improve aroP and develop superior aroP variants.

Example 2: Construction of Modified aroP Library Vector

Based on the vector constructed in Reference Example 1, an aroP-modified library was prepared. To this end, the library was prepared using an error-prone PCR kit (Clontech Diversify® PCR Random Mutagenesis Kit), and the PCR reaction was performed using SEQ ID NO: 8 and SEQ ID NO: 9 as primers under conditions in which mutations could occur.

Specifically, under conditions in which 0 to 3 mutations per 1,000 bp could occur, the PCR reaction was performed such that after pre-heating at 94° C. for 30 seconds, the process at 94° C. for 30 seconds and at 68° C. for 1 minute and 30 seconds was repeated 25 times. At this time, the obtained product was repeatedly subjected to the process at 95° C. for 50 seconds, at 60° C. for 50 seconds, and at 68° C. for 12 minutes using a megaprimer (500 ng to 125 ng) 25 times, then treated with DpnI, transformed into *Escherichia coli* DH5a, and plated on LB solid medium containing kanamycin (25 mg/L). After 20 transformed colonies were selected, a plasmid was obtained, and the polynucleotide sequence was analyzed, and as a result, it was confirmed that mutations were introduced at different locations with a frequency of 2 mutations/kb. About 20,000 transformed *Escherichia coli* colonies were taken and a plasmid was extracted, which was named pTOPO-aroP-library.

Example 3: Preparation of L-Isoleucine-Producing Strain Introduced with aroP Library The pTOPO-aroP-library prepared in Example 2 was transformed into *Corynebacterum glutamicum* CA10-3101 via electroporation, and then plated on a nutrient medium containing kanamycin at 25 mg/L to secure 5,000 colonies of strains into which the mutant gene was inserted, and each of the colonies was named CA10-3101/pTOPO-aroPm1 to CA10-3101/pTOPO-aroPm 5000.

In order to identify colonies by which the L-isoleucine productivity increased and the amount of by-products is reduced among the 5,000 colonies secured, the fermentation potency of each colony was evaluated as follows. The parent strain and the mutant strains were inoculated into 250 mL corner-baffle flasks containing 25 mL of isoleucine production medium, respectively, and then cultured at 32° C. for 60 hours with shaking at 200 rpm to prepare L-isoleucine. The composition of the production medium used in the present Example is as follows.

<Production Medium>

Glucose: 10%, yeast extract: 0.2%, ammonium sulfate: 1.6%, potassium phosphate monobasic: 0.1%, magnesium sulfate heptahydrate: 0.1%, iron sulfate heptahydrate: 10 mg/L, manganese sulfate monohydrate: 10 mg/L, biotin: 200 μg/L, and pH: 7.2

After completion of the culture, the productions of L-isoleucine and L-threonine were measured using high-performance liquid chromatography (HPLC), and the concentrations of L-isoleucine, L-valine, and AABA in the culture of each strain subjected to the experiment are presented in Table 6 below.

TABLE 6

| Strain name | L-Isoleucine concentration (g/L) | AABA concentration (g/L) | L-Valine concentration (g/L) | Ratio of by-products (AABA, L-valine) to isoleucine + by-products |
|---|---|---|---|---|
| CA10-3101 (parent strain) | 2.6 | 0.9 | 1.2 | 0.45 |
| CA10-3101/pTOPO-aroPm138 | 3.0 | 0.6 | 1.2 | 0.38 |
| CA10-3101/pTOPO-aroPm2542 | 2.7 | 0.2 | 0.7 | 0.25 |
| CA10-3101/pTOPO-aroPm3798 | 2.8 | 0.4 | 1.1 | 0.35 |

Ratio of by-products:by-product (AABA, L-valine) concentration/(isoleucine+by-products) concentration As a result, as presented in Table 6, there were identified three strains, which exhibit an increase in L-isoleucine productivity compared to that of *Corynebacterium glutamicum* CA10-3101, the parent strain, and produce by-products AABA and L-valine in a decreased amount compared to the parent strain. Sequencing of the three mutant strains was performed, and the aroP gene was compared with that in wild-type ATCC13032, and as a result, it was confirmed that the three mutant strains contain mutation in the aroP gene.

Specifically, it was confirmed that glycine, the 212th amino acid in the amino acid sequence of aroP, is substituted with threonine (G212T) in the CA10-3101/pTOPO-aroPm138 strain, isoleucine, the 114th amino acid in the amino acid sequence of aroP, is substituted with phenylalanine (I114F) in the CA10-3101/pTOPO-aroPm2542 strain, and alanine, the 28th amino acid in the amino acid sequence of aroP, is substituted with valine (A28V) in the CA10-3101/pTOPO-aroPm3798 strain. Based on the results above, it was confirmed that the three mutant strains can produce L-isoleucine with higher efficiency and higher yield compared to the parent strain. More specifically, when each strain, into which aroP (G212T), aroP (1114), or aroP (A28V) was introduced, was compared to the parent strain, L-isoleucine was produced at a similar concentration, the AABA concentration decreased by about 33%, 78%, and 56%, respectively, the L-valine concentration decreased by about 0%, 42%, and 8%, respectively, and the ratio of by-products (AABA, valine) decreased by 16%, 44%, and 22%, respectively, and it was confirmed that the effect of decreasing the amount of by-products was very excellent in the strains in which aroP (G212T), aroP (I114), or aroP (A28V) was introduced.

Example 4: Preparation of L-Isoleucine-Producing Strain Introduced with Modified aroP The aroP (I114) variant, which has the highest L-isoleucine productivity and reducing rate of by-products among the three types of modified aroP prepared in Example 3, was transformed into *Corynebacterum glutamicum* CA10-3101.

Specifically, as in Reference Example 1, PCR was performed using the chromosome of ATCC13032 as a template and primers of SEQ ID NO: 4 and SEQ ID NO: 5, SEQ ID NO: 6, and SEQ ID NO: 7, or using the chromosomes of pTOPO-aroPm2542 as a template and primers of SEQ ID NO: 8 and SEQ ID NO: 9, respectively. PfuUltra™ high-fidelity DNA polymerase (Stratagene) was used as a polymerase for the PCR reaction, the PCR conditions were denaturation at 95° C. for 30 seconds; annealing at 55° C. for 30 seconds; and polymerization at 72° C. for 1 minute, and the denaturation, annealing, and polymerization were repeated 28 times. As a result, a 1,000 bp DNA fragment at the 5' upstream region and a 1,392 bp DNA fragment at the 3' downstream region were obtained with reference to the gapA promoter portion and aroP gene start codon, respectively. PCR was performed using the three amplified DNA fragments as a template and primers of SEQ ID NO: 4 and SEQ ID NO: 9. As the PCR conditions, denaturation at 95° C. for 5 minutes, then denaturation at 95° C. for 30 seconds; and polymerization at 72° C. for 2 minutes were repeated 6 times, then denaturation at 95° C. for 30 seconds; annealing at 55° C. for 30 seconds; and polymerization at 72° C. for 2 minutes were repeated 20 times, and then polymerization was performed at 72° C. for 5 minutes. As a result, a 2.4 kb DNA fragment encoding the aroP gene including the gapA promoter was amplified. The amplification products were purified using QUIAGEN's PCR purification kit and used as an insert DNA fragment for vector construction. Meanwhile, the insert DNA fragment, which was amplified by the PCR above, were mixed with pDCM2 vector, which was digested with a restriction enzyme SmaI and heat-treated at 65° C. for 20 minutes, at a 1:2 molar ratio (M), and the insert DNA fragment was cloned into the pDCM2 vector TaKaRa's infusion cloning kit according to the manufacturer's manual provided, and thereby a vector pDCM2-PgapA-aroP(I114F), in which the aroP promoter was substituted with the gapA promoter to be introduced into a chromosome, was constructed.

The vectors constructed above were transformed into *Corynebacterium glutamicum* CA10-3101 via electroporation, and followed by a secondary crossover process to obtain strains in which the modified aroP promoter was enhanced and the CA10-3101:PgapA-aroP(I114F) was named CA10-3118. With regard to the L-isoleucine-producing parent strain (CA10-3101), aroP-enhanced strain (CA10-3117) prepared in Example 1, and the strain (CA10-3101) introduced with a variant aroP(I114F) prepared in the present example, the fermentation potency of each strain was evaluated as follows in order to confirm the effect of increasing the L-isoleucine productivity and reducing the amount of by-products. The parent strain and the strains were respectively inoculated into 250 mL corner-baffle flasks containing 25 mL of isoleucine production medium, and then cultured at 32° C. for 60 hours with shaking at 200 rpm to prepare L-isoleucine. The composition of the production medium used in the present Example is as follows.

<Production Medium>

Glucose: 10%, yeast extract: 0.2%, ammonium sulfate: 1.6%, potassium phosphate monobasicn 0.1%, magnesium sulfate heptahydrate: 0.1%, iron sulfate heptahydrate: 10 mg/L, manganese sulfate monohydrate: 10 mg/L, biotin: 200 μg/L, and pH: 7.2

After completion of the culture, the concentrations of L-isoleucine, AABA, and L-valine were measured using high-performance liquid chromatography (HPLC), and the results are presented in Table 7 below.

TABLE 7

| Strain name | L-Isoleucine concentration (g/L) | AABA concentration (g/L) | L-Valine concentration (g/L) | Ratio of by-products (AABA, L-valine) to isoleucine + by-products |
|---|---|---|---|---|
| CA10-3101 (parent strain) | 2.6 | 0.9 | 1.2 | 0.45 |
| CA10-3117 (aroP-enhanced strain) | 2.8 | 0.4 | 1.0 | 0.33 |
| aroP-enhanced and aroP(G212T)-introduced strain | 3.1 | 0.5 | 1.0 | 0.32 |
| CA10-3118 (aroP-enhanced and aroP(I114F)-introduced strain) | 2.8 | 0.2 | 0.7 | 0.24 |
| aroP-enhanced and aroP(A28V)-introduced strain | 3.0 | 0.4 | 0.9 | 0.30 |

Ratio of by-products:by-product (AABA, L-valine) concentration/(isoleucine+by-products) concentration As presented in Table 7, it was confirmed that the amounts of L-isoleucine produced by the aroP-enhanced strain (CA10-3117), aroP(G212T) variant-introduced strain, aroP (I114F) variant-introduced strain (CA10-3118), and aroP (A28V) variant-introduced strain were increased compared to that of the parent strain (CA10-3101), and that the concentrations of by-products (i.e., AABA and L-valine) were decreased compared to those by the parent strain.

Specifically, the amount of L-isoleucine produced by the aroP(G212T)-introduced strain was increased by 15% and 7%, respectively, compared to those of the parent strain and the aroP-enhanced strain; the amount of AABA produced by the aroP(G212T)-introduced strain was decreased by 44% compared to that of the parent strain; and the amount of L-valine produced by the aroP(G212T)-introduced strain was decreased by 20% compared to that of the parent strain.

It was confirmed that the amount of AABA produced by the aroP(I114F) variant-introduced strain was decreased by 88% and 50%, respectively, compared to those of the parent strain and the aroP-enhanced strain; and the amount of L-valine produced by the aroP(I114F) variant-introduced strain was decreased by 42% and 30%, respectively, compared to the parent strain and the aroP-enhanced strain.

It was confirmed that the amount of L-isoleucine produced by the aroP(A28V)-introduced strain was increased by 19% and 11%, respectively, compared to those of the parent strain and the aroP-enhanced strain; the amount of AABA produced by the aroP(A28V)-introduced strain was decreased by 56% compared to that of the parent strain; and the amount of L-valine produced by the aroP(A28V)-introduced strain was decreased by 25% and 10%, respectively, compared to the parent strain and the aroP-enhanced strain.

Additionally, the ratio of the produced amount of by-products (AABA, L-valine) to the produced amount of L-isoleucine and by-products of the aroP(G212T) variant-introduced strain, the aroP(I114F) variant-introduced strain, and the aroP(A28V) variant-introduced strain was decreased by about 29%, 47%, and 33% compared to that of the parent strain, and 3%, 27%, and 9% compared to that of the aroP-enhanced strain, thus confirming that the amount of production of by-products was decreased in the aroP (G212T), aroP(I114F), and aroP(A28V) variant-introduced strains, whereas the L-isoleucine productivity and purity were significantly increased in these strains.

The CA10-3118 strain was internationally deposited with the Korean Culture Center of Microorganisms (KCCM), an international depository under the Budapest Treaty, as of Dec. 1, 2020, and was given a deposit number as KCCM12857P.

Example 5: Construction of aroP-Enhanced Strain and aroP Variant-Introduced Strain from L-Isoleucine Producing Strain The aroP enhancement (introduction of the gapA promoter) and the aroP variants, which show the increase of L-isoleucine production, and reduction of the amount of production of by-products were respectively introduced into the KCJI-38 (KCCM11248P, Korean Registered Patent No. 10-1335789) strain, which was a NTG (N-methyl-N'-nitro-N-nitrosoguanidine)-treated L-isoleucine-producing strain, by way of an electric pulse method, then plated on a selection medium containing kanamycin at 25 mg/L, and transformed, and followed by a secondary crossover process to obtain an aroP-enhanced and aroP modified enhanced strained on the chromosome. Thereafter, the concentrations of L-isoleucine and by-products in the culture were measured in the same manner as in Example 1, and the results are presented in Table 8 below.

TABLE 8

| | L-Isoleucine concentration (g/L) | AABA concentration (g/L) | L-Valine concentration (g/L) | Ratio of by-products (AABA, L-valine) to isoleucine + by-products |
|---|---|---|---|---|
| KCCM11248P (parent strain) | 1.5 | 0.7 | 1.2 | 0.56 |
| KCCM11248PΔPn-aroP::PgapA-aroP | 1.8 | 0.4 | 1.0 | 0.44 |
| KCCM11248PΔPn-aroP::PgapA-aroP(G212T) | 2.0 | 0.4 | 1.1 | 0.43 |
| KCCM11248PΔPn-aroP::PgapA-aroP(I114F) | 1.9 | 0.3 | 0.8 | 0.37 |
| KCCM11248PΔPn-aroP::PgapA-aroP(A28V) | 1.9 | 0.4 | 1.0 | 0.43 |

Ratio of by-products:by-product (AABA, L-valine) concentration/(isoleucine+by-products) concentration As presented in Table 8, it was confirmed that the KCCM11248PΔPn-aroP:PgapA-aroP strain, into which aroP is introduced, showed an increase in the amount of L-isoleucine production and a decrease in the amount of production of by-products compared to those of the parent strain KCCM11248P, whereas the KCCM11248PΔPn-aroP:PgapA-aroP(G212T), KCCM11248PΔPn-aroP:PgapA-aroP(I114F), and KCCM11248PΔPn-aroP:PgapA-aroP(A28V) strains, into which an aroP variant is introduced, showed an increase in the amount of L-isoleucine production compared to KCCM11248P and KCCM11248PΔPn-aroP:PgapA-aroP strains.

The KCCM11248PΔPn-aroP:PgapA-aroP(I114F) strain showed a decrease in the amount of AABA (i.e., a by-product) by about 57% and 25%, and a decrease in the amount of L-valine by about 33% and 20%, compared to KCCM11248P and KCCM11248PΔPn-aroP:PgapA-aroP strains, respectively; and the KCCM11248PΔPn-aroP:PgapA-aroP(G212T) and KCCM11248PΔPn-aroP:PgapA-aroP(A28V) strains showed a decrease in the amount of AABA (a by-product) by about 43% and 43%, and a decrease in the amount of L-valine by about 8% and 17%, compared to KCCM11248P, thus showing a significant increase in the by-product reducing rate.

Additionally, the ratio of the produced amount of by-products (AABA, L-valine) to that of (L-isoleucine+by-products (AABA, L-valine)) for each of the variant strains, the KCCM11248PΔPn-aroP:PgapA-aroP(G212T), KCCM11248PΔPn-aroP:PgapA-aroP(I114F), and KCCM11248PΔPn-aroP:PgapA-aroP(A28V) strains showed a decrease by 23%, 34%, and 2% compared to the parent strain, respectively, and a decrease by 23%, 16%, and 2% compared to the aroP-enhanced strain. Therefore, it was confirmed that the amount of by-product production was significantly decreased in the aroP(G212T), aroP(I114F), or aroP(A28V)-introduced strains while the L-isoleucine productivity and purity thereof were remarkably increased.

From the results above, it was confirmed that the aroP-enhanced strain and variants thereof can increase the amount of L-isoleucine production. In addition, since it was confirmed that the aroP-enhanced strain and variants thereof can contribute to the increase in purity in the production and purification process of L-isoleucine, and it was confirmed that the variations have a role in increasing the production of L-isoleucine.

Based on the above description, it will be understood by those skilled in the art that the present application may be implemented in a different specific form without changing the technical spirit or essential characteristics thereof. Therefore, it should be understood that the above embodiment is not limitative, but illustrative in all aspects. The scope of the disclosure is defined by the appended claims rather than by the description preceding them, and therefore all changes and modifications that fall within metes and bounds of the claims or equivalents of such metes and bounds are therefore intended to be embraced by the claims.

The invention claimed is:

1. A gamma(γ)-aminobutyrate permease variant, wherein
an amino acid at a position corresponding to position 212 of SEQ ID NO: 1 is substituted with threonine,
an amino acid at a position corresponding to position 114 of SEQ ID NO: 1 is substituted with phenylalanine, and/or
an amino acid at a position corresponding to position 28 of SEQ ID NO: 1 is substituted with valine,
wherein the variant comprises a sequence having at least 96% sequence identity to the amino acid sequence of SEQ ID NO: 1.

2. A polynucleotide encoding the variant of claim 1.

3. A vector comprising the polynucleotide of claim 2.

4. A microorganism comprising any one or more of the variant of claim 1; a polynucleotide encoding the variant; and a vector comprising the polynucleotide.

5. The microorganism of claim 4, wherein the microorganism produces L-isoleucine.

6. The microorganism of claim 4, wherein the microorganism is a microorganism of the genus *Corynebacterium.*

7. The microorganism of claim 4, wherein the microorganism is *Corynebacterium glutamicum.*

8. A method for producing L-isoleucine, the method comprising culturing a microorganism comprising one or more of the γ-aminobutyrate permease variant of claim 1; a polynucleotide encoding the variant; and a vector comprising the polynucleotide in a medium.

9. The method for producing L-isoleucine of claim 8, further comprising recovering L-isoleucine from the medium or microorganism.

10. The method for producing L-isoleucine of claim 8, wherein the microorganism is a microorganism of the genus *Corynebacterium.*

11. The method for producing L-isoleucine of claim 8, wherein the method is to decrease an amount of a by-product generated during production of L-isoleucine.

12. The method for producing L-isoleucine of claim 11, wherein the by-product is any one or more selected from the group consisting of α-aminobutyrate (AABA), valine, phenylalanine, and leucine.

13. A method for decreasing an amount of a by-product generated during production of L-isoleucine, the method comprising culturing a microorganism comprising one or more of the γ-aminobutyrate permease variant of claim 1; a polynucleotide encoding the variant; and a vector comprising the polynucleotide in a medium.

14. The γ-aminobutyrate permease variant according to claim 1, wherein the variant comprises a sequence having at least 99% sequence identity to the amino acid sequence of SEQ ID NO: 1.

15. The γ-aminobutyrate permease variant according to claim 1, wherein the variant comprises a sequence having at least 97% sequence identity to the amino acid sequence of SEQ ID NO: 1.

16. The γ-aminobutyrate permease variant according to claim 1, wherein the variant comprises a sequence having at least 98% sequence identity to the amino acid sequence of SEQ ID NO: 1.

17. The γ-aminobutyrate permease variant according to claim 1, wherein the amino acid at the position corresponding to position 212 of SEQ ID NO: 1 is substituted with threonine.

18. The γ-aminobutyrate permease variant according to claim 1, wherein the amino acid at the position corresponding to position corresponding to position 114 of SEQ ID NO: 1 is substituted with phenylalanine.

19. The γ-aminobutyrate permease variant according to claim 1, wherein the amino acid at the position corresponding to position 28 of SEQ ID NO: 1 is substituted with valine.

20. The γ-aminobutyrate permease variant according to claim 1, wherein
the amino acid at the position corresponding to position 212 of SEQ ID NO: 1 is substituted with threonine,
the amino acid at the position corresponding to position 114 of SEQ ID NO: 1 is substituted with phenylalanine, and
the amino acid at the position corresponding to position 28 of SEQ ID NO: 1 is substituted with valine.

* * * * *